(12) United States Patent
Grusby et al.

(10) Patent No.: US 7,314,623 B2
(45) Date of Patent: Jan. 1, 2008

(54) METHODS AND COMPOSITIONS FOR MODULATING T HELPER (TH) CELL DEVELOPMENT AND FUNCTION

(75) Inventors: Michael J. Grusby, Newton, MA (US); Andrea Wurster, Arlington, MA (US); Deborah Young, Melrose, MA (US); Mary Collins, Natick, MA (US); Matthew Whitters, Hudson, MA (US)

(73) Assignee: Wyeth, Madison, NJ (US)

( * ) Notice: Subject to any disclaimer, the term of this patent is extended or adjusted under 35 U.S.C. 154(b) by 326 days.

(21) Appl. No.: 10/620,169

(22) Filed: Jul. 15, 2003

(65) Prior Publication Data

US 2004/0136954 A1    Jul. 15, 2004

Related U.S. Application Data

(60) Provisional application No. 60/396,160, filed on Jul. 15, 2002, provisional application No. 60/403,001, filed on Aug. 12, 2002.

(51) Int. Cl.
*A61K 39/00* (2006.01)
*A61K 39/395* (2006.01)
*A61K 38/17* (2006.01)

(52) U.S. Cl. .............. 424/185.1; 424/143.1; 424/155.1; 514/2; 514/12

(58) Field of Classification Search ............ 514/2; 435/7.2; 436/501, 503
See application file for complete search history.

(56) References Cited

U.S. PATENT DOCUMENTS

| | | | |
|---|---|---|---|
| 3,710,795 A | 1/1973 | Higuchi et al. | |
| 4,816,567 A | 3/1989 | Cabilly et al. | |
| 4,946,778 A | 8/1990 | Ladner et al. | |
| 5,011,912 A | 4/1991 | Hopp et al. | |
| 5,098,833 A | 3/1992 | Lasky et al. | |
| 5,116,964 A | 5/1992 | Capon et al. | |
| 5,155,027 A | 10/1992 | Sledziewski et al. | |
| 5,216,131 A | 6/1993 | Lasky et al. | |
| 5,225,538 A | 7/1993 | Capon et al. | |
| 5,225,539 A | 7/1993 | Winter | |
| 5,262,564 A | 11/1993 | Kun et al. | |
| 5,328,470 A | 7/1994 | Nabel et al. | |
| 5,428,130 A | 6/1995 | Capon et al. | |
| 5,447,851 A | 9/1995 | Beutler et al. | |
| 5,455,165 A | 10/1995 | Capon et al. | |
| 5,514,582 A | 5/1996 | Capon et al. | |
| 5,516,964 A | 5/1996 | Umansky et al. | |
| 5,545,806 A | 8/1996 | Lonberg et al. | |
| 5,545,807 A | 8/1996 | Surani et al. | |
| 5,567,584 A | 10/1996 | Sledziewski et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,714,147 A | 2/1998 | Capon et al. | |
| 5,750,375 A | 5/1998 | Sledziewski et al. | |
| 5,840,844 A | 11/1998 | Lasky et al. | |
| 5,843,725 A | 12/1998 | Sledziewski et al. | |
| 5,916,771 A | 6/1999 | Hori et al. | |
| 5,939,598 A | 8/1999 | Kucherlapati et al. | |
| 6,018,026 A | 1/2000 | Sledziewski et al. | |
| 6,057,128 A | 5/2000 | Donaldson et al. | |
| 6,136,310 A | 10/2000 | Hanna et al. | |
| 6,291,212 B1 | 9/2001 | Sledziewski et al. | |
| 6,291,646 B1 | 9/2001 | Sledziewski et al. | |
| 6,300,099 B1 | 10/2001 | Sledziewski et al. | |
| 6,307,024 B1 | 10/2001 | Novak et al. | |
| 6,323,323 B1 | 11/2001 | Sledziewski et al. | |
| 6,406,697 B1 | 6/2002 | Capon et al. | |
| 6,576,744 B1 | 6/2003 | Presnell et al. | |
| 2002/0090680 A1 | 7/2002 | Hodge ................. 435/69.1 |
| 2002/0128446 A1 | 9/2002 | Novak et al. ............. 530/351 |
| 2002/0137677 A1 | 9/2002 | Sprecher et al. ............. 514/12 |
| 2003/0108549 A1 | 6/2003 | Carter et al. ............. 424/145.1 |
| 2006/0039902 A1 | 2/2006 | Young et al. ............. 424/133.1 |

FOREIGN PATENT DOCUMENTS

| | | |
|---|---|---|
| EP | 0 812 913 A2 | 12/1997 |
| EP | 1 088 831 A1 | 4/2001 |
| WO | WO 93/08829 | 5/1993 |
| WO | WO 94/02602 | 2/1994 |
| WO | WO 96/27011 | 9/1996 |
| WO | WO 96/33735 | 10/1996 |
| WO | WO 96/34096 | 10/1996 |
| WO | WO 97/20926 | 6/1997 |
| WO | WO 97/31946 | 9/1997 |
| WO | WO 97/33913 | 9/1997 |
| WO | WO 97/47741 | 12/1997 |
| WO | WO 97/47742 | 12/1997 |
| WO | WO 98/10638 | 3/1998 |
| WO | WO 98/11225 | 3/1998 |
| WO | WO 98/31811 | 7/1998 |
| WO | WO 99/47675 | 9/1999 |
| WO | WO 99/53049 | 10/1999 |
| WO | WO 00/08152 | 2/2000 |
| WO | WO 00/17235 | 3/2000 |
| WO | WO 00/27882 | 5/2000 |
| WO | WO 00/53761 | 9/2000 |

OTHER PUBLICATIONS

Mijares et al. Molecular Pharmacology, vol. 58, pp. 373-379 2000.*
Heany et al. Journal of Leukocyte Biology, vol. 64, pp. 135-146, Aug. 1998.*
Mehta et al. Immunological Reviews, vol. 202, pp. 84-95, 2004.*
James A. Wells, Sep. 18, 1990, Biochemistry, vol. 29, No. 37, pp. 8509-8517.*

(Continued)

*Primary Examiner*—Eileen O'Hara
*Assistant Examiner*—Fozia Hamud
(74) *Attorney, Agent, or Firm*—Fitzpatrick, Cella, Harper & Scinto

(57) ABSTRACT

Methods and compositions for modulating T helper (Th) cell development and function using modulators of IL-21, e.g., human IL-21, activity or level.

11 Claims, 5 Drawing Sheets

OTHER PUBLICATIONS

Brenne et al. Blood, May 2002. vol. 99, No. 10, pp. 3756-3762.*
Kasaian et al. Immunity, Apr. 2002. vol. 16, pp. 559-569.*
Asao et al. J. Immunol., 167:1-5 (2001).
Bazan J.F. Proc. Natl. Acad. Sci. USA, 87:6934-6938 (1990).
Bird et al. Immunity, 9(2):229-237 (1998).
Biró et al. Immunol. Lett., 46:183-187 (1995).
Brennan et al. Science, 229:81-83 (1985).
Caput et al. J. Biol. Chem., 271(28):16921-16926 (1996).
Chen et al. Proc. Natl. Acad. Sci. USA, 91:3054-3057 (1994).
Cote et al. Proc. Natl. Acad. Sci. USA, 80:2026-2030 (1983).
D'Andrea et al. Cell, 57:277-285 (1989).
Database EMBL, Accession No. AF279436 (Jul. 18, 2000).
Database EMBL, Accession No. AB049137 (Sep. 23, 2000).
Database EMBL, ID HS795114 Accession No. R52795 (May 25, 1995).
Debinski et al. J. Biol. Chem., 270(28):16775-16780 (1995).
Dusanter-Fourt et al. Medecine/Sciences, English Abstract, 10:825-835 (1994).
EMBL Database Accession No. AC002303 (Jun. 26, 1997).
Fishwild et al. Nat. Biotechnol., 14(7):845-851 (1996).
GenBank Database Accession No. M26062 (Jan. 6, 1995).
Gruber et al. J. Immunol., 152(11):5368-5374 (1994).
Hatakeyama et al. Science, 244:551-556 (1989).
Hollinger et al. Proc. Natl. Acad. Sci. USA, 90:6444-6448 (1993).
Hoogenboom et al. J. Mol. Biol., 227:381-388 (1992).
Hopp et al. Proc. Natl. Acad. Sci. USA, 78:3824-3828 (1981).
Huse et al. Science, 246:1275-1281 (1989).
Jones et al. Nature, 321:522-525 (1986).
Kaplan et al. Immunity, 4(3):313-319 (1996).
Kasaian et al. Immunity, 16(4):559-569 (2002).
Köhler et al. Nature, 256:495-497 (1975).
Kostelny et al. J. Immunol., 148(5):1547-1553 (1992).
Kyte et al. J. Mol. Biol., 157(1):105-132 (1982).
Kozbor et al. Immunol. Today, 4(3):72-79 (1983).
Kozbor J. Immunol., 133(6):3001-3005 (1984).
Lai et al. J. Biol. Chem., 270(40):23254-23257 (1995).
Lonberg et al. Nature, 368:856-859 (1994).
Lonberg et al. Int. Rev. Immunol., 13(1):65-93 (1995).
Marks et al. J. Mol. Biol., 222(3):581-597 (1991).
Marks et al. Biotechnol., 10(7):779-783 (1992).
Milstein et al. Nature, 305:537-540 (1983).
Morrison Nature, 368:812-813 (1994).
Munson et al. Anal. Biochem., 107(1):220-239 (1980).
Needleman et al. J. Mol. Biol., 48(3):443-453 (1970).
Neuberger Nat. Biotechnol., 14(7):826 (1996).
O'Dowd et al. Gene, 187(1):75-81 (1997).
Overbergh et al. Cytokine, 11(4):305-312 (1999).
Ozaki et al. Proc. Natl. Acad. Sci. USA, 97(21):11439-11444 (2000).
Page et al. J. Immunol. Methods, 189:129-135 (1996).
Parrish-Novak et al. Nature, 408:57-63 (2000).
Presta Curr. Op. Sturct. Biol., 2(4):593-596 (1992).
Reiner et al. Annu. Rev. Immunol., 13:151-177 (1995).
Riechmann et al. Nature, 332:323-327 (1988).
Shalaby et al. J. Exp. Med., 175:217-225 (1992).
Shimoda et al. Nature, 380:630-633 (1996).
Suresh et al. Meth. Enzymol., 121:210-228 (1986).
Szabo et al. J. Exp. Med., 185(5):817-824 (1997).
Szabo et al. Cell, 100(6):655-669 (2000).
Takeda et al. Nature, 380:627-630 (1996).
Traunecker et al. EMBO J., 10(12):3655-3659 (1991).
Tutt et al. J. Immunol., 147(1):60-69 (1991).
Verhoeyen et al. Science, 239:1534-1536 (1988).
Vita et al. J. Biol. Chem., 270(8):3512-3517 (1995).
Vosshenrich et al. Curr. Biol., 11(5):R157-R177 (2001).
Wilkinson The Scientist, 14(8):25-28 (2000).
Wu et al. J. Immunol., 159:1658-1665 (1997).
Wurster et al. Oncogene, 19(21):2577-2584 (2000).

Yan et al. Science, 290:523-527 (2000).
Zhang et al. J. Biol. Chem., 272(14):9474-9480 (1997).
Bazan "Structural design and molecular evolution of a cytokine receptor superfamily," Proc. Natl. Acad. Sci. USA 87:6934-38 (1990).
Imler et al. "Identification of three adjacent amino acids of interleukin-2 receptor β chain which control the affinity and the specificity of the interaction with interleukin-2," EMBO J. 11:2047-53 (1992).
LaRosa et al. "Amino Terminus of the Interleukin-8 Receptor Is a Major Determinant of Receptor Subtype Specificity," J. Biol. Chem. 267:25402-06 (1992).
Schimmenti et al. "Localization of an essential ligand binding determinant of the human erythropoietin receptor to a domin N-terminal to the WSXWS motif: implications for soluble receptor function," Exp. Hematol. 23:1341-46 (1995).
Mulhern et al. "The Solution Structure of the Cytokine-binding Domain of the Common β-Chain of the Receptors for Granulocyte-Macrophage Colony-stimulating Factor, Interleukin-3 and Interleukin-5," J. Mol. Biol. 297:989-1001 (2000).
Woodcock et al. "Three residues in the common β chain of the human GM-CSF, IL-3 and IL-5 receptors are essential for GM-CSF and IL-5 but not IL-3 high affinity binding and interact with Glu21 of GM-CSF," EMBO J. 13:5176-85 (1994).
Blast 2 Sequences Results comparing GenBank Accession Nos. Q9JHX3 and NP_068570, entitled "Amino Acid Sequence comparison of Mouse and Human IL-21R", printed Apr. 6, 2006., Novak et al.
Blast 2 Sequences Results comparing GenBank Accession Nos. NP_068570 and AAA59143, entitled "Amino Acid Sequence comparison of Human IL-21R and Human IL-2Rβ," printed Apr. 6, 2006., Hatakeyama et al.
GenBank Accession No. Q9JHX3 "Interleukin-21 receptor precursor (IL-21R)" (Mouse) Parrish-Novak et al. (2000), printed on Nov. 1, 2006.
GenBank Accession No. AAA59143 "Interleukin 2 receptor beta chain precursor peptide" Hatakeyama et al. (1998), printed on Nov. 1, 2006.
GenBank Accession No. NP_068570, "Interleukin 21 receptor precursor [Homo Sapiens]" Parrish-Novak et al. (2000), printed on Apr. 2, 2007.
Site Directed Mutagenesis § 20-3 (pp. 738-744) in Basic Methods in Molecular Biology, $2^{nd}$ Edition (1994) Davis et al. (Eds.) Appleton & Lange, CT.
Gearing and Thorpe (1988) "The International Standard for Human Interleukin-2" J. Immunol. Meth. 114:3-9.
Yokota et al. (1985) "Use of a cDNA Expression Vector for Isolation of Mouse Interleukin 2 cDNA Clones: Expression of T-Cell Growth-Factor Activity after Transfection of Monkey Cells" Proc. Natl. Acad. Sci. U.S.A. 82 (1): 68-72.
Fukushima and Yamashita (Mar. 2001) "Interleukin-2 Carbohydrate Recognition Modulates CTLL-2 Cell Proliferation" J. Biol. Chem. 276:7351-56.
Taylor (1986) "The classification of amino acid conservation" J. Theor. Biol. 119:205-18.
Zvelebil et al. (1987) "Prediction of protein secondary structure and active sites using the alignment of homologous sequences" J. Mol. Biol. 195:957-61.
Iwata et al. (2003) "A Broad-Spectrum Caspase Inhibitor Attenuates Allergic Airway Inflammation in Murine Asthma Model" J. Immunol. 170:3386-91.
Kinoshita et al. (2000) "Costimulation by B7-1 and B7-2 is required for autoimmune disease in MRL-Fas$^{lpr}$ mice" J. Immunol. 164:6046-56.
Myers et al. (1997) "Collagen-Induced Arthritis, An Animal Model of Autoimmunity" Life Sciences 61:1861-78.

* cited by examiner

FIGS 1A-1D
A.
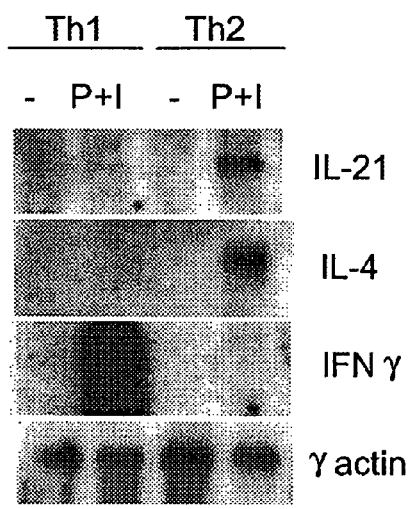
B.
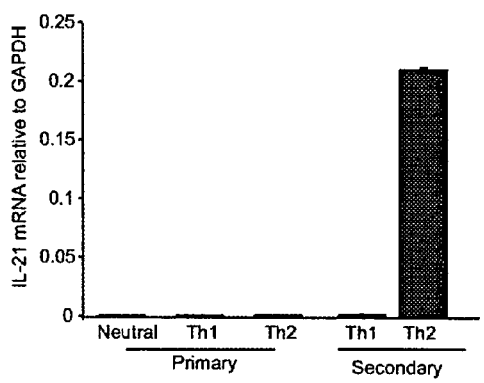
C.
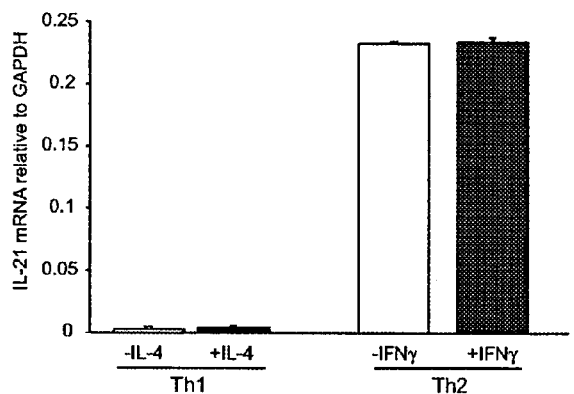
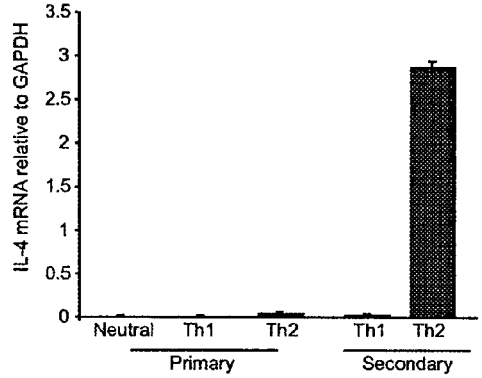
D.
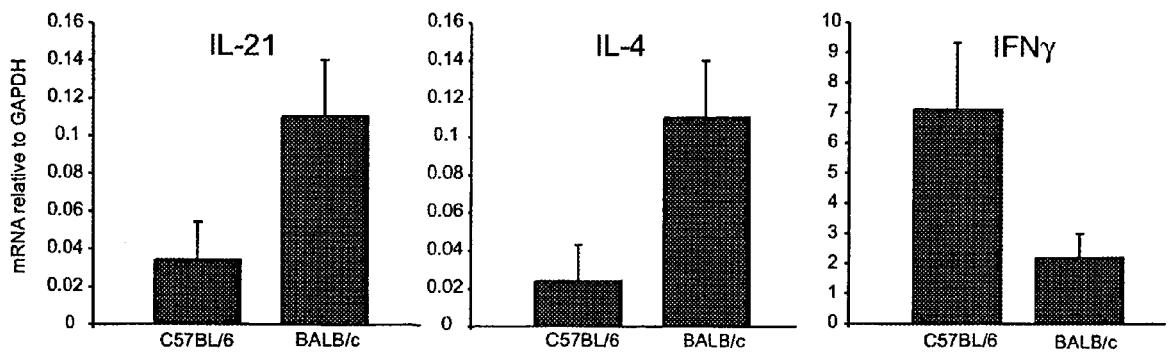

A.

B.

METHODS AND COMPOSITIONS FOR MODULATING T HELPER (TH) CELL DEVELOPMENT AND FUNCTION

RELATED APPLICATIONS

This application claims the benefit of U.S. Provisional Application No. 60/396,160, filed Jul. 15, 2002, and U.S. Provisional Application No. 60/403,001, filed Aug. 12, 2002, both of which are hereby incorporated by reference herein in their entireties.

STATEMENT AS TO FEDERALLY SPONSORED RESEARCH

This invention was made with Government support under a grant from the National Institutes of Health number AI40171. The Government has certain rights in the invention.

FIELD OF THE INVENTION

The invention relates to modulators of IL-21, e.g., human IL-21, activity or levels and their uses in modulating T cell, e.g., T helper (Th) cell, development and function.

BACKGROUND OF THE INVENTION

T helper (Th) subsets are distinguished by their ability to produce distinct cytokine patterns and promote specific immune responses. Th1 cells produce IFNγ and promote cell-mediated immunity directed towards intracellular pathogens. In contrast, Th2 cells produce the cytokines IL-4, IL-5, and IL-13, activate mast cells and eosinophils and direct B cells against extracellular pathogens. Dysregulation of Th responses can result in immunopathology in that aberrant Th1 responses can be responsible for organ-specific autoimmunity, and exaggerated Th2 responses have been associated with allergic diseases.

The specific cytokines produce by polarized Th cells are the primary effectors that promote differentiation of precursor Th (Thp) cells, but these cells also cross-regulate the other subset's functional activity. For example IL-4 is reported to be a potent factor in promoting the differentiation of Thp cells to Th2 effectors. In addition, IL-4 antagonizes production of IFNγ. IL-10, another cytokine produced by Th2 cells, has also been described to inhibit Th1 development and IFNγ-induced macrophage function. Conversely, the IFNγ produced by Th1 cells amplifies Th1 development and inhibits the expansion of Th2 cells. The ability of these cytokines to promote development of specific Th cell subsets, while simultaneously inhibiting the alternate developmental fate, results in progressively polarized response.

SUMMARY OF THE INVENTION

The invention is basedin part on the discovery that the cytokine interleukin-21 (IL-21) is expressed by a subset of T helper (Th) cells, Th2 cells, and selectively inhibits interferon γ (IFNγ) levels during Th1 cell development. More specifically, it is herein shown that IL-21 is preferentially expressed by Th2 cells generated in vitro and in vivo. In one embodiment, exposure of developing Th cells to IL-21 specifically reduced IFNγ levels from developing Th1 cells, and thus potentiated Th2 responses. In addition, exposure of developing Th cells to IL-21 reduces Stat4 signaling, e.g., by reducing Stat4 protein and/or mRNA expression, thereby modulating Th cell responsiveness to other cytokines, e.g., IL-12. Thus, methods and compositions for modulating Th cell development and activity are disclosed. The methods and compositions, e.g., agonists or antagonists of IL-21, described herein are useful in treating (e.g., curing, ameliorating, delaying or preventing the onset of, or preventing recurrence or relapse of), or preventing, Th cell- and/or IFNγ- associated disorders or conditions, such as Th2-associated disorders, e.g., asthma, allergy, and disorders associated with antibody components (e.g., rheumatoid arthritis, multiple sclerosis and lupus); and Th1-associated disorders, e.g., autoimmune disorders (e.g., multiple sclerosis, rheumatoid arthritis, type I diabetes, Crohn's disease, psoriasis and myasthenia gravis, among others).

In one aspect, the invention features a method for inhibiting, e.g., reducing or eliminating, interferon gamma (IFNγ) levels in a T cell or cell population. The method provides, for example, inhibiting IFNγ activity, expression, secretion, or processing in a T cell, e.g., a T cell precursor cell (a Thp cell), or a Th1 cell (e.g., a differentiating Th1 cell or an effector Th cell), or in a T cell population thereof. The method includes contacting the T cell or cell population with an IL-21 agonist in an amount sufficient to inhibit IFNγ (e.g., reduce or eliminate) in the T cell or cell population, such that the agonist is an IL-21 polypeptide comprising an amino acid sequence which is at least 85% identical to SEQ ID NO: 2, and which is capable of binding to an IL-21R. In some embodiments, the method further includes identifying a T cell or cell population in which inhibition of IFNγ levels is desired.

In another aspect, the invention features a method for promoting differentiation of a Th precursor (Thp) cell or cell population into a Th2 cell or cell population. In one embodiment, the method includes contacting the Thp cell or cell population with an IL-21 agonist in amount sufficient to induce differentiation of the Thp cell or cell population into a Th2 cell or cell population, and the agonist is an IL-21 polypeptide having an amino acid sequence that is at least 85% identical to SEQ ID NO: 2 and which is capable of binding to an IL-21R. In some embodiments, the method further includes identifying a Thp cell or cell population in which differentiation into a Th2 cell or cell population is desired.

In another aspect, the invention features a method of inhibiting differentiation of a Thp cell or cell population into a Th1 cell or cell population. The method includes contacting the Thp cell or cell population with an IL-21 agonist in an amount sufficient to inhibit differentiation of the Thp cell or cell population into a Th1 cell or cell population, and the agonist is an IL-21 polypeptide having an amino acid sequence that is at least 85% identical to SEQ ID NO: 2 and which is capable of binding to an IL-21R. In one embodiment, this method further includes identifying a T cell population in which inhibition of differentiation of the Thp cell or cell population into a Th1 cell or cell population is desired.

In some embodiments of these methods, the polypeptide includes the amino acid sequence of SEQ ID NO:2. In some embodiments of these methods, the contacting step is carried out ex vivo, in vitro, or in vivo. A suitable subject for ex vivo or in vivo methods includes a mammalian subject, for example, a human.

In another aspect, the invention features a method for inhibiting differentiation of a Th precursor (Thp) cell or cell population into a Th2 cell or cell population. The method includes contacting the Thp cell or population with an antagonist of an interleukin-21 (IL-21 )/IL-21 receptor (IL- 21 R) in an amount sufficient to inhibit differentiation of the Thp cell or cell population into the Th2 cell population, and the antagonist is selected from the group consisting of an anti-IL-21R antibody, an antigen-binding fragment of an anti-IL-21R antibody and a soluble fragment of an IL-21R. The method optionally further includes identifying a T cell or cell population in which inhibition of differentiation of a Thp cell or cell population into a Th2 cell or cell population is desired. In some embodiments, the T cell population includes at least one Th1 cell.

In some embodiments, the soluble fragment of an IL-21R includes an extracellular region of an IL-21 Receptor. For example, the soluble fragment can include an amino acid sequence at least 85% identical to amino acids 20 to 235 of SEQ ID NO: 4 and which is capable of binding IL-21; alternatively, the soluble fragment includes amino acids 1 to 235 of SEQ ID NO:4. In related embodiments, the soluble fragment further includes an Fc fragment. In yet another embodiment, the antagonist is an anti-IL-21R antibody or an antigen-binding fragment of the anti-IL-21R antibody.

In yet another embodiment, the contacting step is carried out ex vivo, in vitro or in vivo. The contacting step can be carried out in a mammalian subject, for example, the mammalian subject is a human.

In another aspect, the invention features a method for increasing interferon gamma (IFNγ) levels in a T cell or cell population. The method in one embodiment includes contacting the T cell or cell population with an antagonist of an IL-21/IL-21R in an amount sufficient to increase IFNγ levels in the T cell or cell population, and the antagonist is selected from the group consisting of an anti-IL-21R antibody, an antigen-binding fragment of an anti-IL-21R antibody and a soluble fragment of an IL-21R. An embodiment of this method further includes identifying a T cell population in which an increase in IFNγ levels is desired.

In some embodiments, the soluble fragment of an IL-21R includes an extracellular region of an IL-21 Receptor. For example, in some embodiments the soluble fragment comprises an amino acid sequence at least 85% identical to amino acids 20 to 235 of SEQ ID NO:4 and which is capable of binding IL-21; alternatively, the soluble fragment includes amino acids 1 to 235 of SEQ ID NO:4. In related embodiments, the soluble fragment further includes an Fc fragment. In yet another embodiment, the antagonist can be an anti-IL-21R antibody or an antigen-binding fragment of the anti-IL-21R antibody.

In yet another related embodiment, the contacting step is carried out ex vivo, in vitro or in vivo. In some embodiments, the contacting step is performed in a mammalian subject, for example, a human.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A is a representation of a Northern blot hybridization analysis examining expression of IL-21, IL-4, IFNγ, and γ actin under the various Th1 and Th2 skewing conditions described in the appended Examples.

FIG. 1B is a histogram showing the level of IL-21 mRNA relative to GAPDH mRNA in Th1 and Th2 cells following primary and secondary stimulation.

FIG. 1C is a histogram showing the level of IL-21 mRNA relative to GAPDH mRNA in primary and secondary Th1 and Th2 cells cultured in the presence or absence of IL-4 and IFNγ.

FIG. 1D is a histogram showing the level of IL-21 mRNA, IL-4 mRNA, and IFNγ mRNA relative to GAPDH mRNA in C57BL/g and BALB/c mice following infection with L. major.

DETAILED DESCRIPTION OF THE INVENTION

Figure 2A:
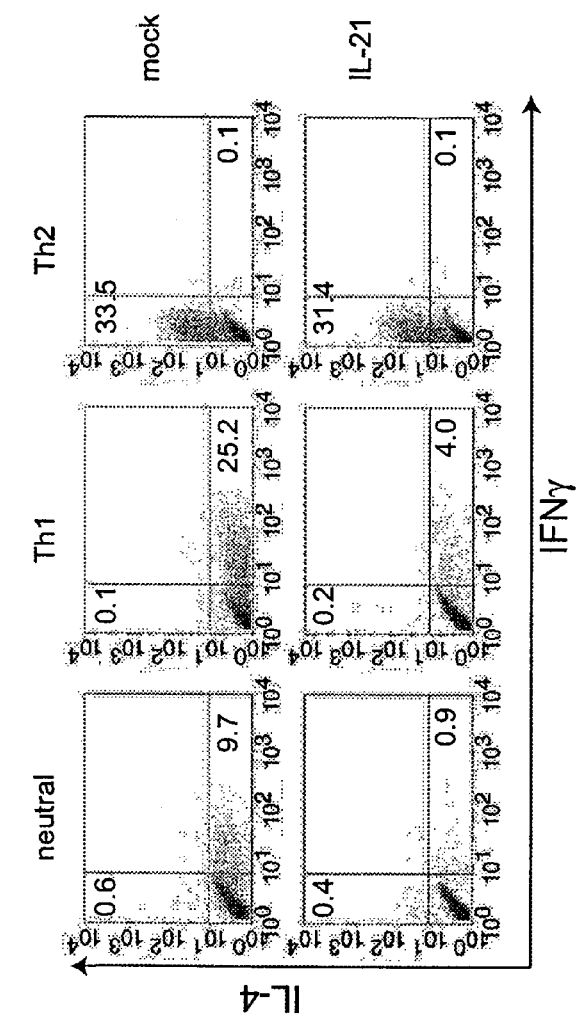
FIG. 2A is a graphic representation of IL-4 and IL-21 cytokine production in Thp cells cultured under neutral conditions, or Th1 skewing conditions.

The invention provides methods and compositions for modulating T helper cell differentiation, development and activity by modulating the interaction between IL-21 and an IL-21 receptor. IL-21, or agents that increase IL-21 or IL-21 receptor levels in a cell population, are added to a population of T helper cells to suppress IFNγ levels in a population of Thp or Th1 cells. IL-21, or agents that increase IL-21 levels, can also be used to promote Th2 development, or to potentiate Th2-mediated immune responses and/or to suppress Th1 development.

IL-21, or agents that increase IL-21 levels, can also be used to inhibit the effects of IL-12 on the T helper cell population. IL-21 or agents that increase levels of IL-21 or otherwise act as IL-21 agonists, can be used to suppress Th1 mediated diseases such as autoimmune diseases, multiple sclerosis, rheumatoid arthritis, and type I diabetes.

In one aspect, the invention features a method for modulating, e.g., increasing, or reducing or inhibiting, the activity or level of interferon gamma (IFNγ) in a cell, e.g., a T cell, or a cell population, e.g., a T cell population. For example, a method for modulating one or more of: IFNγ activity, expression, secretion, or processing, in a T cell, e.g., a T cell precursor cell (a Thp cell), or a Th1 cell (e.g., a differentiating Th1 cell or an effector Th cell), or a T cell population thereof, is provided. The method includes:

(optionally) identifying a cell, e.g., a T cell, or a cell population, e.g., a T cell population, in which modulation (e.g., increase or reduction) of the activity or level of IFNγ is desired; and contacting said cell or cell population with an amount of an IL-21 modulator, e.g., an IL-21 agonist or antagonist, sufficient to modulate (e.g., increase or reduce) the activity or level of IFNγ in said cell or cell population.

The subject method can be used on cells in culture, e.g. in vitro or ex vivo. For example, immune cells, e.g., T cells as described herein, can be cultured in vitro in culture medium and the contacting step can be effected by adding one or more IL-21 modulators (e.g., an IL-21 agonist or antagonist), to the culture medium. Alternatively, the method is performed on cells (e.g., immune or T cells as described herein) present in a subject, e.g., as part of an in vivo (e.g., therapeutic or prophylactic) protocol.

In one embodiment, a method for reducing or inhibiting the activity or level of IFNγ in a cell, e.g., a T cell (e.g., a T cell precursor cell (a Thp cell), or a Th1 cell (e.g., a differentiating Th1 cell or an effector Th cell)), or a cell population thereof is provided. The method includes (optionally) identifying a cell, e.g., a T cell, or a cell population, e.g., a T cell population, in which reduction or inhibition of the activity or level of IFNγ is desired; and contacting said cell or cell population with an amount of an IL-21 agonist, sufficient to reduce or inhibit the activity or level of IFNγ in said cell or cell population. Preferably, the IL-21 agonist specifically inhibits WNy levels or activity, e.g., it does not reduce or inhibit the activity or level of other cytokines such IL-2 or TNFα. In one embodiment, the IL-21 agonist inhibits production of IFNγ by an TFNγ-producing cell, e.g., an IFNγ-producing Th1 cell.

In other embodiments, the invention provides a method for reducing IFNγ levels or activity in a subject. The method includes (optionally) identifying a subject in which reduction of IFNγ levels or activity is desired; and administering to said subject an amount of an IL-21 agonist sufficient to reduce the levels or activity IFNγ. IFNγ can be measured using techniques known in the art, for example, intracellular cytokine staining, or an ELISA technique to determine levels in cell supernatants.

The IL-21 agonist can be an IL-21 polypeptide, a human IL-21 polypeptide, or an active fragment thereof (e.g., a human IL-21 polypeptide comprising the amino acid sequence shown as SEQ ID NO:2, or encoded by a nucleotide sequence shown as SEQ ID NO:1, or a sequence substantially homologous thereto). In other embodiments, the IL-21 agonist is a fusion protein comprising an IL-21 polypeptide, e.g., human IL-21 polypeptide, or a fragment thereof fused to another polypeptide, e.g., an immunoglobulin polypeptide or a portion thereof (e.g., an Fc region of an immunoglobulin polypeptide); an agonist antibody to the IL-21 receptor; or a small molecule agonist. In other embodiments, the IL-21 agonist is an agent that increases the activity or level of IL-21 by, e.g., increasing expression, processing and/or secretion of functional IL-21.

Preferably, the subject is a mammal, e.g., a human subject suffering from a disorder associated with aberrant, e.g., increased, IFNγ levels or activity, e.g., an immune disorder (e.g., a T cell-mediated disorder), in an amount sufficient to ameliorate or prevent said disorder.

Exemplary immune disorders that can be treated (e.g., ameliorated) or prevented using agonists of IL-21 include, for example, Th1-associated disorders, such as autoimmune disorders (including, but not limited to, multiple sclerosis, rheumatoid arthritis, type 1 diabetes, inflammatory bowel disease (IBD), psoriasis and myasthenia gravis.

The invention additionally features a method of increasing IFNγ levels or activity in a cell, e.g., a T-cell, or a cell population, e.g., a T cell population. For example, the invention includes method for increasing IFNγ activity, expression, secretion, or processing, in a T cell, e.g., a T cell precursor cell (a Thp cell), or a Th1 cell (e.g., a differentiating Th1 cell or an effector Th cell), or a T cell population thereof. The method includes (optionally) identifying a cell, e.g., a T cell, or cell population, e.g., a T cell population, in which an increase in IFNγ expression is desired; and contacting said cell with an IL-21 antagonist in an amount sufficient to inhibit binding or activity of IL-21, e.g., inhibit binding of IL-21 to an IL-21 receptor, thereby increasing IFNγ expression levels in said cell.

The IL-21 antagonist can be, e.g., an antibody (e.g., a monoclonal or single specificity antibody) to IL-21, e.g., human IL-21, or an IL-21 receptor, e.g., human IL-21 receptor polypeptide. Preferably, the antibody is a human, humanized, chimeric, or in vitro generated antibody to human IL-21 or human IL-21 receptor polypeptide. In other embodiments, the antagonist includes a fragment of an IL-21 polypeptide, e.g., an IL-21 receptor binding domain of an IL-21 polypeptide. Alternatively, the antagonist includes a fragment of an IL-21 receptor polypeptide, e.g., an IL-21 binding domain of an IL-21 receptor polypeptide. In one embodiment, the antagonist is a fusion protein comprising the aforesaid IL-21 or Il-21 receptor polypeptides or fragments thereof fused to a second moiety, e.g., a polypeptide (e.g., an immunoglobulin chain).

In another aspect, the invention features a method for modulating, e.g., increasing or decreasing, Th2 cell activity and/or cell number. In one embodiment, a method of modulating, e.g., promoting or inhibiting, one or more of proliferation, survival and/or differentiation into (e.g., differentiation of a T cell precursor, e.g., a Th precursor (Thp), into) a Th2 cell is provided. The method includes:

(optionally) identifying a cell, e.g., a T cell (e.g., a Thp or a Th2 cell), or a cell population, where modulation of proliferation, survival and/or differentiation is desired; and contacting said cell or cell population with an IL-21 modulator, e.g., an IL-21 agonist or antagonist, in an amount sufficient to modulate one or more of proliferation, survival and/or differentiation into (e.g., modulating differentiation of said Thp cell into a Th2 cell) a Th2 cell, thereby modulating Th2 cell activity and/or cell number.

The subject method can be used on cells in culture, e.g. in vitro or ex vivo. For example, immune cells, e.g., T cells as described herein, can be cultured in vitro in culture medium and the contacting step can be effected by adding one or more IL-21 modulators (e.g., one or more IL-21 agonists or antagonists) to the culture medium. Alternatively, the method can be performed on cells (e.g., immune or T cells as described herein) present in a subject, e.g., as part of an in vivo (e.g., therapeutic or prophylactic) protocol.

In one embodiment, a method of reducing or inhibiting Th2 cell activity and/or cell number is provided. For example, Th2 cell activity and/or cell number can be reduced or inhibited by inhibiting or reducing one or more of proliferation, survival and/or differentiation into (e.g., differentiation of a T cell precursor, e.g., a Th precursor (Thp), into) a Th2 cell. The method includes (optionally) identifying a cell, e.g., a T cell (e.g., a Thp or a Th2 cell), or a cell population, where inhibition of proliferation, survival and/or differentiation is desired; and contacting said cell or cell population with an IL-21 antagonist in an amount sufficient to inhibit or reduce one or more of proliferation, survival and/or differentiation into (e.g., inhibiting or reducing differentiation of said Thp cell into a Th2 cell) a Th2 cell, thereby inhibiting or reducing Th2 cell activity and/or cell number.

The subject method can be used on cells, e.g., T cells (e.g., Thp or Th2 cells) in culture, e.g. in vitro or ex vivo.

Alternatively, the method can be performed on cells (e.g., immune or T cells as described herein) present in a subject, e.g., as part of an in vivo (e.g., therapeutic or prophylactic) protocol. For example, the method can be used to treat or prevent a Th2-mediated disorder, e.g., asthma and allergy, in a subject. Accordingly, the invention provides a method of treating (e.g., curing, suppressing, ameliorating, delaying or preventing the onset of, or preventing recurrence or relapse of) or preventing a Th2-associated disorder in a subject. The method includes administering to a subject an IL-21 antagonist in an amount sufficient to inhibit or reduce Th2 cell activity and/or cell number, thereby treating or preventing a Th2-associated disorder.

Preferably, the subject is a mammal, e.g., a human suffering from a disorder associated with aberrant Th2 cell number or activity, e.g., an immune disorder (e.g., a Th2-associated disorder). The amount sufficient to inhibit or reduce the cell activity and/or number is an amount sufficient to ameliorate or prevent said disorder.

The IL-21 antagonist can be, e.g., an antibody (e.g., a monoclonal or single specificity antibody) to IL-21, e.g., human IL-21, or an IL-21 receptor, e.g., human IL-21 receptor polypeptide. Preferably, the antibody is a human, humanized, chimeric, or in vitro generated antibody to human IL-21 or human IL-21 receptor polypeptide. In other embodiments, the antagonist includes a fragment of an IL-21 polypeptide, e.g., an IL-21 receptor binding domain of an IL-21 polypeptide. Alternatively, the antagonist includes a fragment of an IL-21 receptor polypeptide, e.g., an IL-21 binding domain of an IL-21 receptor polypeptide. In one embodiment, the antagonist is a fusion protein comprising the aforesaid IL-21 or Il-21 receptor polypeptides or fragments thereof fused to a second moiety, e.g., a polypeptide (e.g., an immunoglobulin chain).

In yet another embodiment, a method of increasing Th2 cell activity and/or cell number is provided. For example, Th2 cell activity and/or cell number can be increased by increasing one or more of proliferation, survival and/or differentiation into (e.g., differentiation of a T cell precursor, e.g., a Th precursor (Thp), into), a Th2 cell. The method includes (optionally) identifying a cell, e.g., a T cell (e.g., a Thp or a Th2 cell), or a cell population, where increased proliferation, survival and/or differentiation is desired; and contacting said cell or cell population with an IL-21 agonist in an amount sufficient to increase one or more of proliferation, survival and/or differentiation into, (e.g., increase differentiation of said Thp cell into a Th2 cell) a Th2 cell, thereby increasing Th2 cell activity and/or cell number.

The IL-21 agonist can be an IL-21 polypeptide, e.g., a human IL-21 polypeptide, or an active fragment thereof (e.g., a human IL-21 polypeptide comprising the amino acid sequence shown as SEQ ID NO:2, or encoded by a nucleotide sequence shown as SEQ ID NO:1, or a sequence substantially homologous thereto). In other embodiments, the IL-21 agonist is a fusion protein comprising an IL-21 polypeptide, e.g., human IL-21 polypeptide, or a fragment thereof fused to another polypeptide, e.g., an immunoglobulin polypeptide or a portion thereof (e.g., an Fc region of an immunoglobulin polypeptide); an agonist antibody to the IL-21 receptor; or a small molecule agonist.

In yet another aspect, a method for modulating, e.g., increasing or decreasing, Th1 cell number and/or activity is provided. In one embodiment, a method of modulating, e.g., promoting or inhibiting, one or more of proliferation, survival and/or differentiation into (e.g., differentiation of a T cell precursor, e.g., a Th precursor (Thp), into), a Th1 cell is provided. The method includes (optionally) identifying a cell, e.g., a T cell (e.g., a Thp or a Th1 cell), or a cell population, where modulation of proliferation, survival and/or differentiation is desired; and contacting said cell or cell population with an IL-21 modulator, e.g., an agonist or an antagonist, in an amount sufficient to modulate one or more of proliferation, survival and/or differentiation into, (e.g., modulate differentiation of said Thp cell into a Th1 cell) a Th1 cell, thereby modulating Th1 cell activity and/or cell number.

The subject method can be used on cells in culture, e.g. in vitro or ex vivo. For example, immune cells, e.g., T cells as described herein, can be cultured in vitro in culture medium and the contacting step can be effected by adding one or more IL-21 modulators (e.g., an IL-21 agonist or antagonist), to the culture medium. Alternatively, the method can be performed on cells (e.g., immune or T cells as described herein) present in a subject, e.g., as part of an in vivo (e.g., therapeutic or prophylactic) protocol.

In one embodiment, a method of reducing or inhibiting Th1 cell activity and/or cell nurmlber is provided. For example, Th1 cell activity and/or cell number can be reduced or inhibited by inhibiting or reducing one or more of proliferation, survival and/or differentiation into (e.g., differentiation of a T cell precursor, e.g., a Th precursor (Thp), into), a Th1 cell. The method includes (optionally) identifying a cell, e.g., a T cell (e.g., a Thp, a cell producing IFNγ, e.g., a Th1 cell), or a cell population, where inhibition of proliferation, survival and/or differentiation is desired; and contacting said cell or cell population with an IL-21 agonist in an amount sufficient to inhibit or reduce one or more of proliferation, survival and/or differentiation into, (e.g., inhibiting or reducing differentiation of said Thp cell into a Th1 cell) a Th1 cell, thereby inhibiting or reducing Th1 cell activity and/or cell number.

The subject method can be used on cells, e.g., T cells (e.g., Thp or Th2 cells) in culture, e.g. in vitro or ex vivo.

Alternatively, the method can be performed on cells (e.g., immune or T cells as described herein) present in a subject, e.g., as part of an in vivo (e.g., therapeutic or prophylactic) protocol. For example, the method can be used to treat or prevent a Th1-mediated disorder, e.g., an autoimmune disorder (e.g., multiple sclerosis, rheumatoid arthritis, type I diabetes, Crohn's disease, psoriasis and myasthenia gravis, among others), in a subject. Accordingly, the invention provides a method of treating (e.g., curing, suppressing, ameliorating, delaying or preventing the onset of, or preventing recurrence or relapse of) or preventing a Th1-associated disorder in a subject. The method includes administering to a subject an IL-21 agonist in an amount sufficient to inhibit or reduce Th1 cell activity and/or cell number, thereby treating or preventing a Th1-associated disorder.

Preferably, the subject is a mammal, e.g., a human suffering from a disorder associated with aberrant Th1 cell number or activity, e.g., an immune disorder (e.g., a Th1-associated disorder as described herein). An amount sufficient to inhibit or reduce TH1 cell activity and/or cell member is an amount sufficient to ameliorate or prevent said disorder.

The IL-21 agonist can be an IL-21 polypeptide, e.g., a human IL-21 polypeptide, or an active fragment thereof (e.g., a human IL-21 polypeptide comprising the amino acid sequence shown as SEQ ID NO:2, or encoded by a nucleotide sequence shown as SEQ ID NO:1, or a sequence substantially homologous thereto). In other embodiments, the IL-21 agonist is a fusion protein comprising an IL-21 polypeptide, e.g., human IL-21 polypeptide, or a fragment thereof fused to another polypeptide, e.g., an immunoglobulin polypeptide or a portion thereof (e.g., an Fc region of an immunoglobulin polypeptide); an agonist antibody to the IL-21 receptor; or a small molecule agonist. In other embodiments, the IL-21 agonist is an agent that increases the activity or level of IL-21 by, e.g., increasing expression, processing and/or secretion of functional IL-21.

In yet another embodiment, a method of increasing Th1 cell activity and/or cell number is provided. For example, Th1 cell activity and/or cell number can be increased by increasing one or more of proliferation, survival and/or differentiation into (e.g., differentiation of a T cell precursor, e.g., a Th precursor (Thp), into), a Th1 cell. The method includes:

(optionally) identifying a cell, e.g., a T cell (e.g., a Thp or a Th1 cell), or a cell population, where increased proliferation, survival and/or differentiation is desired; and contacting said cell or cell population with an IL-21 antagonist in an amount sufficient to increase one or more of proliferation, survival and/or differentiation into, (e.g., increase differentiation of said Thp cell into a Th1 cell) a Th1 cell, thereby increasing Th1 cell activity and/or cell number.

The IL-21 antagonist can be, e.g., an antibody (e.g., a monoclonal or single specificity antibody) to IL-21, e.g., human IL-21, or an IL-21 receptor, e.g., human IL-21 receptor polypeptide. Preferably, the antibody is a human, humanized, chimeric, or in vitro generated antibody to human IL-21 or human IL-21 receptor polypeptide. In other embodiments, the antagonist includes a fragment of an IL-21 polypeptide, e.g., an IL-21 receptor binding domain of an IL-21 polypeptide. Alternatively, the antagonist includes a fragment of an IL-21 receptor polypeptide, e.g., an IL-21 binding domain of an IL-21 receptor polypeptide. In one embodiment, the antagonist is a fusion protein comprising the aforesaid IL-21 or Il-21 receptor polypeptides or fragments thereof fused to a second moiety, e.g., a polypeptide (e.g., an immunoglobulin chain).

In yet another aspect, the invention features a method of modulating, e.g., reducing or inhibiting, or increasing, interleukin-12 (IL-12) activity or level in a cell, cell population, or a subject. The method includes:

(optionally) identifying a cell, e.g., a T cell, cell population or subject, where modulation of IL-12 is desired; and contacting said cell or cell population with, or administering to said subject, an IL-21 modulator, e.g., an agonist or an antagonist of IL-21, in an amount sufficient to modulate IL-12 activity or level in said cell, cell population, or a subject.

In one embodiment, the activity or level of IL-12 is/are reduced by contacting said cell or cell population, or administering to said subject, an IL-21 agonist, e.g., an IL-21 agonist as described herein, in an amount sufficient to reduce the activity or levels of IL-12.

In other embodiments, the activity or level of IL-12 is/are increased by contacting said cell or cell population, or administering to said subject, an IL-21 antagonist, e.g., an IL-21 antagonist as described herein, in an amount sufficient to increase the activity or level of IL-12.

In yet another aspect, the invention features a method of modulating, e.g., reducing or inhibiting, or increasing, Stat, e.g., Stat 4, activity or level in a cell, cell population, or a subject. The method includes:

(optionally) identifying a cell, e.g., a T cell, cell population or subject, where modulation of Stat activity or level is desired; and contacting said cell or cell population with, or administering to said subject, an IL-21 modulator, e.g., an agonist or an antagonist of IL-21, in an amount sufficient to modulate Stat activity or level in said cell, cell population, or a subject.

In one embodiment, the activity or level of Stat is reduced by contacting said cell or cell population, or administering to said subject, an IL-21 agonist, e.g., an IL-21 agonist as described herein, in an amount sufficient to reduce the activity or level of Stat, e.g., Stat protein or mRNA.

In other embodiments, the activity or level of Stat is increased by contacting said cell or cell population, or administering to said subject, an IL-21 antagonist, e.g., an IL-21 antagonist as described herein, in an amount sufficient to increase the activity or level of Stat, e.g., Stat protein or mRNA.

In yet another aspect, the invention features a method of decreasing, inhibiting, suppressing, ameliorating, or delaying an autoimmune response (e.g., a Th1-mediated autoimmune response), in a subject. The method includes administering to a subject in need thereof an IL-21 agonist, e.g., an IL-21 agonist as described herein, in an amount sufficient to decrease, inhibit, suppress, ameliorate, or delay said autoimmune response in said subject.

In yet another aspect, the invention features a method of decreasing, inhibiting, suppressing, ameliorating, or delaying a Th2-associated response (e.g., an allergic or an asthmatic response), in a subject. The method includes administering to a subject in need thereof an IL-21 antagonist, e.g., an IL-21 antagonist as described herein, in an amount sufficient to decrease, inhibit, suppress, ameliorate, or delay said Th2-associated response in said subject.

In another aspect, the invention features a method of selectively identifying a Th2 cell in a cell population, e.g., a Th cell population, the method comprising determining the levels of IL-21 nucleic acid (e.g., an IL-21 gene product) or polypeptide in a test sample, e.g., a Th cell, and a reference sample, e.g., a Th1 cell; and comparing the levels of said IL-21 nucleic acid in said test sample to levels of said IL-21 nucleic acid in the reference sample, e.g., the Th1 cell, wherein an increase in levels of said IL-21 nucleic acid in said test sample relative to said reference sample indicates the test sample is a Th2 cell.

As used herein, a "Th1-associated disorder" is a disease or condition associated with aberrant, e.g., increased or decreased, Th1 cell activity (e.g., increased or decreased Th1 cell responses) or number compared to a reference, e.g., a normal control. Examples of Th1-associated disorders include, e.g., autoimmune disorders (e.g., multiple sclerosis, rheumatoid arthritis, type I diabetes, Crohn's disease, psoriasis and myasthenia gravis, among others).

As used herein, a "Th2-associated disorder" is a disease or condition associated with aberrant, e.g., increased or decreased, Th2 cell activity (e.g., increased or decreased Th2 cell responses) or number compared to a reference, e.g., a normal control. Examples of Th2 disorders include, e.g., asthma, allergy, and disorders associated with antibody components (e.g., rheumatoid arthritis, multiple sclerosis and lupus).

The IL-21 polypeptide used in the methods described herein can include the amino acid sequence of, e.g., a mammalian IL-21 polypeptide (such as a rodent, human, or non-human primate). For example, the IL-21 polypeptide can include the amino acid sequence of a human IL-21 polypeptide. A suitable amino acid sequence is the amino acid sequence of the IL-21 polypeptide shown in SEQ ID NO:2 (below).

IL-21 and IL-21 receptor polypeptides, including nucleotide and amino acid sequences, have been described in, e.g., U.S. Pat. No. 6,057,128, Parrish-Novak et al., Nature 408:57-63, 2000; Vosshenrich et al., Curr. Biol. 11:R157-77,2001, Asao et al., J. Immunol. 167:1-5, 2001; and Ozaki et al., Proc. Natl. Acad. Sci. USA 97:11439-44,2000. Amino acid sequences of IL-21 polypeptides are publicly known. For example, the nucleotide sequence and amino acid sequence of a human IL-21 is available at Genbank Acc. No. X_011082. The human IL-21 nucleotide sequence disclosed in this entry is presented below:

```
  1 gctgaagtga aaacgagacc aaggtctagc tctactgttg gtacttatga gatccagtcc    (SEQ ID NO:1)

61 tggcaacatg gagaggattg tcatctgtct gatggtcatc ttcttgggga cactggtcca 121 caaatcaagc tcccaaggtc aagatcgcca catgattaga atgcgtcaac ttatagatat 181 tgttgatcag ctgaaaaatt atgtgaatga cttggtccct gaatttctgc cagctccaga 241 agatgtagag acaaactgtg agtggtcagc tttttcctgc tttcagaagg cccaactaaa 301 gtcagcaaat acaggaaaca atgaaaggat aatcaatgta tcaattaaaa agctgaagag 361 gaaaccacct tccacaaatg cagggagaag acagaaacac agactaacat gcccttcatg 421 tgattcttat gagaaaaaac cacccaaaga attcctagaa agattcaaat cacttctcca 481 aaagatgatt catcagcatc tgtcctctag aacacacgga agtgaagatt cctgaggatc 541 taacttgcag ttggacacta tgttacatac tctaatatag tagtgaaagt catttctttg 601 tattccaagt ggaggag
```

The amino acid sequence encoded by the disclosed human IL-21 nucleic acid sequence is presented below:

```
MRSSPGNMERIVICLMVIFLGTLVHKSSSQGQDRHMIRMRQLIDIVDQLKNYVNDLVPEF    (SEQ ID NO:2)

LPAPEDVETNCEWSAFSCFQKAQLKSANTGNNERIINVSIKKLKRKPPSTNAGRRQKHRL

TCPSCDSYEKKPPKEFLERFKSLLQKMIHQHLSSRTHGSEDS.
```

The nucleotide sequence of a human IL-21 receptor nucleic acid is provided below:

```
  1 gaagcagcag gtaccccctc cacatcccta gggctctgtg atgtaggcag aggcccgtgg    (SEQ ID NO:3)

61 gagtcagcat gccgcgtggc tgggccgccc ccttgctcct gctgctgctc cagggaggct 121 ggggctgccc cgacctcgtc tgctacaccg attacctcca gacggtcatc tgcatcctgg 181 aaatgtggaa cctccacccc agcacgctca cccttacctg gcaagaccag tatgaagagc 241 tgaaggacga ggccacctcc tgcagcctcc acaggtcggc ccacaatgcc acgcatgcca 301 cctacacctg dcacatggat gtattccact tcatggccga cgacattttc agtgtcaaca 361 tcacagacca gtctggcaac tactcccagg agtgtggcag ctttctcctg ctgagagca 421 tcaagccggc tccccctttc aacgtgactg tgaccttctc aggacagtat aatatctcct 481 ggcgctcaga ttacgaagac cctgccttct acatgctgaa gggcaagctt cagtatgagc 541 tgcagtacag gaaccggga gacccctggg ctgtgagtcc gaggagaaag ctgatctcag
```

-continued

```
 601 tggactcaag aagtgtctcc ctcctccccc tggagttccg caaagactcg agctatgagc
 661 tgcaggtgcg ggcagggccc atgcctggct cctcctacca ggggacctgg agtgaatgga
 721 gtgacccggt catctttcag acccagtcag aggagttaaa ggaaggctgg aaccctcacc
 781 tgctgcttct cctcctgctt gtcatagtct tcattcctgc cttctggagc ctgaagaccc
 841 atccattgtg gaggctatgg aagaagatat gggccgtccc cagccctgag cggttcttca
 901 tgccctgta caagggctgc agcggagact caagaaatg gtgggtgca cccttcactg
 961 gctccagcct ggagctggga ccctggagcc cagaggtgcc ctccaccctg gaggtgtaca
1021 gctgccaccc accacggagc ccggccaaga ggctgcagct cacggagcta caagaaccag
1081 cagagctggt ggagtctgac ggtgtgccca gcccagcttc tggccgaca gcccagaact
1141 cgggggctc agcttacagt gaggagaggg atcggcccata cggcctggtg tccattgaca
1201 cagtgactgt gctagatgca gagggggccat gcacctggcc ctgcagctgt gaggatgacg
1261 gctacccagc cctggacctg gatgctggcc tggagcccag cccaggccta gaggacccac
1321 tcttggatgc agggaccaca gtcctgtcct gtggctgtgt ctcagctggc agccctgggc
1381 taggagggcc cctgggaagc ctcctggaca gactaaagcc acccttgca gatggggagg
1441 actgggctgg gggactgccc tggggtggcc ggtcacctgg aggggtctca gagagtgagg
1501 cgggctcacc cctggccggc ctggatatgg acacgtttga cagtggcttt gtgggctctg
1561 actgcagcag ccctgtggag tgtgacttca ccagccccgg ggacgaagga ccccccggga
1621 gctacctccg ccagtggtg gtcattcctc cgccactttc gagccctgga ccccaggcca
1681 gctaatgagg ctgactggat gtccagagct ggccaggcca ctgggccctg agccagagac
1741 aaggtcacct gggctgtgat gtgaagacac ctgcagcctt tggtctcctg gatgggcctt
1801 tgagcctgat gtttacagtg tctgtgtgtg tgtgtgcata tgtgtgtgtg tgcatatgca
1861 tgtgtgtgtg tgtgtgtgtc ttaggtgcgc agtggcatgt ccacgtgtgt gtgtgattgc
1921 acgtgcctgt gggcctggga taatgcccat ggtactccat gcattcacct gccctgtgca
1981 tgtctggact cacggagctc acccatgtgc acaagtgtgc acagtaaacg tgtttgtggt
2041 caacagatga caacagccgt cctccctcct agggtcttgt gttgcaagtt ggtccacagc
2101 atctccgggg ctttgtggga tcagggcatt gcctgtgact gaggcggagc ccagccctcc
2161 agcgtctgcc tccaggagct gcaagaagtc catattgttc cttatcacct gccaacagga
2221 agcgaaaggg gatggagtga gcccatggtg acctcgggaa tggcaatttt ttgggcggcc
2281 cctggacgaa ggtctgaatc ccgactctga taccttctgg ctgtgctacc tgagccaagt
2341 cgcctcccct ctctgggcta gagtttcctt atccagacag tggggaaggc atgacacacc
2401 tgggggaaat tggcgatgtc acccgtgtac ggtacgcagc ccagagcaga ccctcaataa
2461 acgtcagctt ccttccttct gcggccagag ccgaggcggg cgggggtgag aacatcaatc
2521 gtcagcgaca gcctgggcac ccgcggggcc gtcccgcctg cagagggcca ctcgggggg
2581 tttccaggct taaaatcagt ccgtttcgtc tcttggaaac agctccccac caaccaagat
2641 ttctttttct aacttctgct actaagtttt taaaaattcc ctttatgcac ccaagagata
2701 tttattaaac accaattacg tagcaggcca tggctcatgg gacccacccc ccgtggcact
2761 catggagggg gctgcaggtt ggaactatgc agtgtgctcc ggccacacat cctgctgggc
2821 cccctaccct gccccaattc aatcctgcca ataaatcctg tcttatttgt tcatcctgga
2881 gaattga
```

The disclosed IL-21 receptor nucleic acid sequence encodes a polypeptide with the following amino acid sequence:

```
MPRGWAAPLLLLLLQGGWGCPDLVCYTDYLQTVICILEMWNLHPSTLTLTWQDQYEELKDEATSCSLHRSAHNATHAT    (SEQ ID NO:4)

YTCHMDVFHFMADDIFSVNITDQSGNYSQECGSFLLAESIKPAPPFNVTVTFSGQYNISWRSDYEDPAFYMLKGKLQY

ELQYRNRGDPWAVSPRRKLISVDSRSVSLLPLEFRKDSSYELQVRAGPMPGSSYQGTWSEWSDPVIFQTQSEELKEGW

NPHLLLLLLLVIVFIPAFWSLKTHPLWRLWKKIWAVPSPERFFMPLYKGCSGDFKKWVGAPFTGSSLELGPWSPEVPS

TLEVYSCHPPRSPAKRLQLTELQEPAELVESDGVPKPSFWPTAQNSGGSAYSEERDRPYGLVSIDTVTVLDAEGPCTW

PCSCEDDGYPALDLDAGLEPSPGLEDPLLDAGTTVLSCGCVSAGSPGLGGPLGSLLDRLKPPLADGEDWAGGLPWGGR

SPGGVSESEAGSPLAGLDMDTFDSGFVGSDCSSPVECDFTSPGDEGPPRSYLRQWVVIPPPLSSPGPQAS
```

The nucleic acid sequence homology may be determined as the degree of identity between two nucleotide or amino acid sequences. The homology may be determined using computer programs known in the art, such as GAP software provided in the GCG program package. See, *Needleman and Wunsch* 1970 *J Mol Biol* 48: 443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1 or SEQ ID NO:3. Similarly the amino acid sequences referred to herein exhibit a degree of identity preferably of at least 50%, 60%, 70%, 75%, 80%, 85%, 90%, 95%, 98%, or 99%, with the amino acid sequence shown in SEQ ID NO:4, SEQ ID NO:5 or SEQ ID NO:6.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 98 or 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Agents that increase IL-21 or IL-21 receptor levels in a cell or cell population can additionally include IL-21 agonists or IL-21 receptor agonists. Such agonists can be identified by identifying test compounds that exert one or more of the activities IL-21 exerts on T helper cell populations.

The subject can be a mammal, e.g., a human, a non-human primate, a dog, cat, cow, horse, pig or a rodent (including a rat or mouse). Any desired route of administration of IL-21 can be used. Suitable routes include intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions.

IL-21 Antagonists

To inhibit an IL-21 mediated T helper cell effect, an agent that blocks or otherwise inhibits the interaction of IL-21 to an IL-21 receptor can be added to a T cell or a population of T cells, e.g., T helper cells. For convenience, these inhibitors are referred to herein as "IL-21 antagonists." Examples of IL-21 antagonists include, e.g., soluble fragments of IL-21 or IL-21 receptors, fusion proteins containing these fragments, and antibodies to these fragments. IL-21 antagonists are useful for blocking IL-21 in Th2 mediated disease, including antibody-mediated disease. Theses diseases include asthma, allergy, rheumatoid arthritis, multiple sclerosis, and lupus.

IL-21 and IL-21 Receptor Fusion Proteins

IL-21, or IL-21 receptor, or active fragments of these proteins, can be fused to carrier molecules such as immunoglobulins for use in the herein described methods. For example, soluble forms of the IL-21 receptor may be fused through "linker" sequences to the Fc portion of an immunoglobulin or to the Fc portion of the immunoglobulin. Other fusions proteins, such as those with GST (i.e., glutathione S-transferase), LexA, or MBP (i.e., maltose binding protein), may also be used.

In a further embodiment, IL-21 or IL-21 receptor fusion protein may be linked to one or more additional moieties. For example, the IL-21 or IL-21 receptor fusion protein may additionally be linked to a GST fusion protein in which the IL-21 receptor fusion protein sequences are fused to the C-terminus of the GST sequences. Such fusion proteins can facilitate the purification of the IL-21 or IL-21 receptor fusion protein.

In another embodiment, the fusion protein includes a heterologous signal sequence (i.e., a polypeptide sequence that is not present in a polypeptide naturally encoded by an IL-21 or IL-21 receptor nucleic acid) at its N-terminus. For example, the native IL-21 or IL-21 receptor signal sequence can be removed and replaced with a signal sequence from another protein.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary-overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). An IL-21 or IL-21 receptor encoding nucleic acid can be cloned into such an expression vector such that the fusion moiety is linked in-frame to the immunoglobulin protein.

polypeptides are known in the art and are described in e.g., U.S. Pat. Nos. 5,516,964; 5,225,538; 5,428,130; 5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light chain, Fab, Fab$_2$, Fv, or Fc. Preferably, the second polypeptide includes the heavy chain of an immunoglobulin polypeptide. More preferably, the second polypeptide includes the Fc region of an immunoglobulin polypeptide.

In some embodiments, the second polypeptide has less effector function than the effector function of a Fc region of a wild-type immunoglobulin heavy chain. Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

A preferred second polypeptide sequence includes the amino acid sequence of SEQ ID NO: 6. This sequence includes a Fc region. Underlined amino acids are those that differ from the amino acid found in the corresponding position of the wild-type immunoglobulin sequence:

HTCPPCPAPE<u>A</u>LG<u>A</u>PSVFLFPPKPKDTLMISRTPEVTCVVVDVSHEDPEVKFNWYVDGVEVHNAK (SEQ ID NO:6)

TKPREEQYNSTYRVVSVLTVLHQDWLNGKEYKCKVSNKALP<u>V</u>PIEKTISKAKGQPREPQVYTLPP

SREEMTKNQVSLTCLVKGFYPSDIAVEWESNGQPENNYKTTPPVLDSDGSFFLYSKLTVDKSRWQ

QGNVFSCSVMHEALHNHYTQKSLSLSPGK

In some embodiments, the IL-21 or IL-21 receptor polypeptide moiety is provided as a variant IL-21 receptor polypeptide having a mutation in the naturally-occurring IL-21 or IL-21 receptor sequence (wild type) that results in higher affinity (relative to the non-mutated sequence) binding of the altered IL-21 for an IL-21 receptor, or higher affinity (relative to the non-mutated sequence) of the altered IL-21 receptor polypeptide for IL-21.

In some embodiments, the IL-21 polypeptide or IL-21 receptor polypeptide moiety is provided as a variant IL-21 or IL-21 receptor polypeptide having mutations in the naturally-occurring IL-21 or IL-21 receptor sequence (wild type) that results in an IL-21 or IL-21 receptor sequence more resistant to proteolysis (relative to the non-mutated sequence).

A signal peptide that can be included in the fusion protein is MPLLLLLLLLPSPLHP (SEQ ID NO:5). If desired, one or more amino acids can additionally be inserted between the first polypeptide moiety comprising the IL-21 or IL-21 receptor moiety and the second polypeptide moiety.

The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second IL-21 receptor polypeptide. In preferred embodiments, the second polypeptide includes at least a region of an immunoglobulin polypeptide. Immunoglobulin fusion IL-21 and IL-21 Receptor Antibodies The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, e.g., polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain. Reference herein to antibodies includes a reference to all such classes, subclasses and types of human antibody species. Antibodies to IL-21 or IL-21 receptor polypeptides also include antibodies to fusion proteins containing IL-21 or IL-21 receptor polypeptides or fragments of IL-21 or IL-21 receptor polypeptides.

An IL-21 polypeptide or IL-21 receptor polypeptide can be used as an antigen, or a portion or fragment thereof, and additionally can be used as an immunogen to generate antibodies that immunospecifically bind the antigen, using standard techniques for polyclonal and monoclonal antibody preparation. Antigenic peptide fragments of the antigen for use as immunogens include, e.g., at least 7 amino acid residues of the amino acid sequence of the amino terminal region, such as an amino acid sequence shown in SEQ ID NOs:1 or 3, and encompass an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the aritigenic peptide are regions of the protein that are located on its surface; commonly these are hydrophilic regions.

In some embodiments, at least one epitope encompassed by the antigenic peptide is a region of IL-21 or IL-21 receptor polypeptide that is located on the surface of the protein, e.g., a hydrophilic region. A hydrophobicity analysis of a IL-21 or IL-21 receptor polypeptide will indicate which regions of an IL-21 or IL-21 receptor protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods (1981) Proc. Nat. Acad. Sci. USA 78: 3824-3828; Kyte and Doolittle (1982) J. Mol. Biol. 157: 105-142. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof. See, for example, ANTIBODIES: A LABORATORY MANUAL, Harlow and Lane (1988) Cold Spring Harbor Laboratory Press, Cold Spring Harbor, N.Y. Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor.

The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by Wilkinson. Wilkinson (2000) The Scientist, 14: 25-28.

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein (1975) Nature, 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, MONOCLONAL ANTIBODIES: PRINCIPLES AND PRACTICE, Academic Press, (1986) pp. 59-103. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parenteral cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) J. Immunol., 133:3001; Brodeur et al., MONOCLONAL ANTIBODY PRODUCTION TECHNIQUES AND APPLICATIONS, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem., 107:220. Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison (1994) Nature 368, 812-13) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These, antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al. (1986) Nature, 321:522-525; Riechmann et al. (1988) Nature, 332: 323-327; Verhoeyen et al. (1988) Science, 239:1534-1536), by substituting rodent CDRs or CDR sequences for the corresponding sequences of a human antibody. (See also U.S. Pat. No. 5,225,539. ) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta (1992) Curr. Op. Struct. Biol., 2:593-596).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al. (1983) Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the invention and may be produced by using human hybridomas (see Cote, et al. (1983) Proc Natl Acad Sci USA 80: 2026-2030) or by transforming human B-cells with Epstein Barr Virus in vitro (see Cole, et al. (1985) In: MONOCLONAL ANTIBODIES AND CANCER THERAPY, Alan R. Liss, Inc., pp. 77-96).

In addition; human antibodies can also be produced using additional techniques, including phage display libraries. See Hoogenboom and Winter (1991) J. Mol. Biol., 227:381; Marks et al. (1991) J. Mol. Biol., 222:581. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al., (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. See PCT publication WO94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al. (1989) Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. (Milstein and Cuello (1983) Nature, 305:537-539. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, and in Traunecker et al. (1991) EMBO J., 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al. (1986) Methods in Enzymology, 121:210.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g F(ab')$_2$ bispecific antibodies). Techniques for generating bispecific antibodies from antibody fragments have been described in the literature. For example, bispecific antibodies can be prepared using chemical linkage. Brennan et al. (1985) Science 229:81 describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al. (1992) J. Exp. Med. 175:217-225 describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al. (1992) J. Immunol. 148(5):1547-1553. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (1993) Proc. Natl. Acad. Sci. USA 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber etal. (1994) J. Immunol. 152:5368.

Antibodies with more than two valencies are contemplated. For example, trispecific antibodies can be prepared. Tutt et al. (1991) J. Immunol. 147:60.

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Pharmaceutical Compositions

The IL-21 modulators described herein can be conveniently provided in pharmaceutical compositions. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the compounds or their pharmaceutically acceptable salts, are administered in amounts which will be sufficient to effect the desired change, i.e., an increase or decrease in IL-21 levels, and are used in the pharmaceutical form most suitable for such purposes.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

The compounds of the invention can also be administered in such oral dosage forms as timed release and sustained release tablets or capsules, pills, powders, granules, elixers, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the invention may also be delivered by the use of monoclonal antibodies as individual carriers to which the compound molecules are coupled. The compounds of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). Pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the invention range from 0.002 mg to 50 mg per kg of body weight per day.

Compounds of the invention may be administered in a single daily dose, or the total daily dosage may be administered in divided doses of two, three or four times daily.

Any of the above pharmaceutical compositions may contain 0.1-99%, preferably 1-70% of the IL-21, IL-21 receptor, IL-21 agonist, or IL-21 antagonist.

If desired, the pharmaceutical compositions can be provided with an adjuvant. Adjuvants are discussed above. In some embodiments, adjuvants can be used to increase the immunological response, depending on the host species, include Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Generally, animals are injected with antigen using several injections in a series, preferably including at least three booster injections.

The invention will be further illustrated in the following non-limiting examples. Examples 1-8 were performed using the following materials and methods.

EXAMPLES

Mice

Unless indicated otherwise, C57BL/6 mice of 6-8 weeks of age were used in all experiments. Stat6-deficient mice on C57BL/6-deficient background were generated as described in Kaplan, M. H., et al., Immunity 4: 313-9, 1996.

Lymphocyte Preparation and Culture

Lymphocytes were cultured in RPMI 1640 supplemented as described in (Kaplan, M. H., et al., Immunity 4: 313-9, 1996). Naïve Thp cells were purified from lymph node and spleens by cell sorting using anti-CD4 and anti-CD26L (Pharmingen; BD Life Sciences, San Diego, Calif.) to 95-98% purity.

Antibodies and Cytokines

T-bet specific antiserum was prepared as described in (Szabo, S. J. et al., Cell 100: 655-69, 2000). Antibodies specific for Stat4, Stat1, and actin were obtained from Santa Cruz Biotechnology (Santa Cruz, Calif.). An antibody specific for phosphorylated Stat4 was obtained from Zymed (South San Francisco, Calif.). The antibodies to anti-CD3, and-CD28, IL-4, and IFNγ used in Th differentiation cultures were obtained from Pharmingen. Recombinant IL-4 was obtained from Preprotech. Recombinant IL-2 was provided by Chiron (Emeryville, Calif.). Recombinant IL-12 was provided by Hoffman-LaRoche (Nutley, N.J.). Mouse IL-21 expressed in COS supernatants was prepared and concentrated. One unit of activity was defined as the concentration of supernatent required to induce 50% maximal proliferation of BAF3 cells transfected with IL-21R. Mock transfected COS supernatent, prepared and concentrated in parallel with IL-21, was used as a control.

In Vitro T Helper Cell Differentiation

Naïve T cells were plated onto anti-CD3, anti-CD28 (1 μg/ml) coated plates at 1-2×10$^6$/ml in the presence of 10 ng/ml IL-4, 10 μg/ml anti-IFNγ (Th2 conditions) or 1 ng/ml IL-12, 10 μg/ml anti IL-4 (Th1 conditions). Cells were expanded in IL-2 (100 U/ml) three days later. After one week in culture, the cells were stimulated with PMA/Ionomycin, and cytokine production was determined by intracellular cytokine staining as described in (Bird, J. J. et al., Immunity 9: 229-37, 1998).

RNA Analysis

Total RNA was isolated using RNeasy (Qiagen; Valencia, Calif.). For northern analysis, the RNA was separated on a 1.5% agarose/6% formaldehyde gel and transferred to Gene-Screen membrane (New England Nuclear). The membrane was hybridized with radiolabeled cDNA probes for IL-21, Il-4, IFNγ, γ-actin. For RealTime PCR, 1 μg of RNA was primed with oligo (dT) and converted to cDNA using Superscript (Invitrogen Life Technologies; Carlsbad, Calif.). 25 ng of cDNA was used as template in PCR reations using SYBR Green 2× or TaqMan 2×PCR mix (Applied Biosystems; Foster City, Calif.) and analyzed in the ABI Prism 7700 Sequence Detector (Applied Biosystems) using the following primers:

Il-21 forward; 5'aagattcctgaggatccgagaag-3' (SEQ ID NO:7)
IL-21 reverse: 5'gcattcgtgagcgtctatagtgtc-3' (SEQ ID NO:8)
IL-21 TaqMan probe: 5'ttcccgaggactgaggagacgcc-3' (SEQ ID NO:9)
IL-12Rγ2 forward: 5'tttccatttttgcatcaagttctc3' (SEQ ID NO:10)
IL-12Rγ2 reverse: 5'ccgatctagagtcagccgct 3' (SEQ ID NO:11)
Stat4 forward: 5'aaacctgagcccaacgacaa3' (SEQ ID NO:12)
Stat4 reverse: 5'agtgtccgtttgcaccgtc3' (SEQ ID NO:13)

Primers and TaqMan probes for IL-4, IFNγ, and GAPDH have been published previously (Overbergh, L., et al., Cytokine 11: 305-121999).

Immunoblot Analysis

Whole cell extracts were prepared by lysing cells in 50 mM Tris, 0.5% NP40, 5 mM EDTA, 50 mM NaCl and clearing the lysates by centrifugation. Protein extracts were separated on an 8-10% polyacrylamide gel and transferred to an Optitran membrane (Schleicher and Schuell; Keene, N. H.). The immunoblots were blocked for one hour at room temperature in 5% milk in TBST (50 mM Tris Ph 7.5, 100 mM NaCl, 0.03% Tween 20) and incubated with the indicated antibody overnight at 4 degrees Centigrade. The blots were washed with TBST and incubated with anti-rabbit HRP-conjuguated antibody (Zymed) at room temperature. After washing the blots with TBST, detection was performed using enhanced chemiluminescence (Amersham; Piscataway, N.J.) according to the manufacturer's instructions.

Example 1

IL-21 is Preferentially Expressed in Th Cells Induced to Develop along Th2 Pathway in vitro Expression of IL-21 in Th subsets was determined. Northern analysis was performed on mRNA from naive Thp (Th precursor) cells differentiated into Th1 or Th2 cells for one week and restimulated for four hours to induce cytokine production. The results are shown in FIGS. 1A-1D. For the results shown in FIG. 1A, Thp cells were cultured under Th1 and Th2 skewing conditions for 6 days. The cells were left resting (−) or restimulated with PMA/Ionomycin (P+I) for 4 hours. RNA was purified and assessed for cytokine expression by Northern blot. The results shown are representative of three independent experiments. Message encoding IL-21 was detected only in stimulated Th2 cells, and in contrast IL-21 message was undetectable in Th1 cultures. These results indicate that IL-21 is a Th2-specific cytokine.

To determine whether the potential to express IL-21 increases as cells develop along a Th2 pathway, IL-21 expression in primary stimulated Thp cells was compared to IL-21 message expression in secondary stimulated Th2 cells. The results are shown in FIG. 1B. For the results shown, Thp cells were cultured under neutral, Th1 and Th2 skewing conditions. RNA was purified 24 hours after primary and secondary anti-CD3 stimulation. Cytokine expression was assessed in duplicate by RealTime PCR and shown relative to GAPDH. IL-21 message, like IL-4, was observed to be relatively low in Thp cells after primary stimulation. In contrast, IL-21 expression was markedly increased after cells were allowed to differentiate along the Th2 pathway. These results demonstrate that IL-21 gene expression is regulated similarly to other Th2-specific cytokines.

The effect of cytokine milieu on IL-21 expression in differentiated cells was determined. Th1 and Th2 cells were cultured in the presence of IL-4 and IFNγ, respectively, before secondary stimulation. Cells were responsive to these cytokines as evidenced by the activation of Stat6 and Stat1 by IL-4 and IFNγ.

The ability of IL-4 to restore IL-21 expression was examined. The results are shown in FIG. 1C. Thp cells were cultured under Th1 and Th2 skewing conditions for 5 days. IL-4 or IFNγ were added to indicated cultures 24 hours prior to secondary stimulation with anti-CD3. RNA was purified 24 hours after secondary stimulation and IL-21 expression was assessed in duplicate relative to GAPDH by RealTime PCR. Addition of IL-4 to Th1 cells was not able to restore IL-21 expression to the level seen in Th2 cells. Moreover, the addition of IFNγ to the Th2 cultures had no inhibitory effect on the expression of IL-21. These results demonstrate that expression of IL-21 in Th2 cells appears to be fixed early in Th2 differentiation and is not modulated directly by IL-4 or IFNγ.

Example 2

Th2 Cells Express IL-21 during a Th2 Immune Response in vivo

The expression of IL-21 in Th2 cells during an in vivo immune response was determined in a pathogenic protozoan model system. Infection with the protozoan *Leishmania major* provides a well-characterized model for studying the in vivo response of Th cells (Reiner, S. L., et al., Annu Rev Imrnunol 13: 151-77, 1995). Some inbred mouse strains, such as C57BL/6, infected with *L. major* mount a protective and effective Th1 response against the pathogen. Conversely, other inbred mouse strains, such as BALB mouse strains, develop primarily a Th2 response and fail to clear the infection.

Both C57BL/6 and BALB/c mice were infected with *L. major*. Cohorts of 8 BALB/c and C57BL/6 mice were infected with *L. major* in hind footpads. After 6 weeks CD4+ T cells from draining lymph nodes were purified and stimulated with anti-CD3. RNA was purified 6 hours after stimulation and cytokine expression was assessed relative to GAPDH by RealTime PCR.

The results are shown in FIG. 1D. As expected, CD4+ cells from C57BL/6 infected mice expressed more IFNγ than cells from BALB/c infected mice. Consistent with a predominantly Th2 response, CD4+ T cells from infected BALB/c mice made significantly more IL-4 than T cells from C57BL/6 mice. Similar to what was observed under in vitro Th2 skewing conditions, IL-21 was also preferentially expressed during an in vivo Th2 response in BALB/c mice. These results, combined with in vitro findings (Example 1), demonstrate that IL-21 is a Th2 cytokine.

Example 3

IL-21 Specifically Inhibits Production of IFNγ in Developing Th Cells

Because IL-21 shares a similar expression profile in Th cells as well as structural similarity to IL-4, the ability of IL-21, like IL-4, to influence Th differentiation directly was determined.

To determine the effect of IL-21 on Thp differentiation, Thp cells were cultured under neutral, Th1 and Th2 skewing conditions.

Purified naive Thp cells were primed under neutral, Th 1, and Th2 skewing conditions in the presence and absence of IL-21. The cytokine potential of these cells was assessed by intracellular cytokine staining after one week in culture.

Figure 2B:
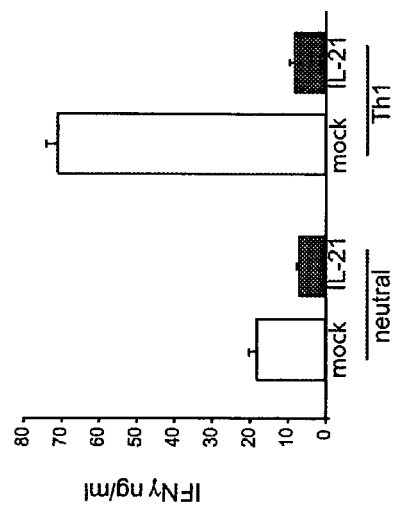
FIG. 2B is a histogram showing IFNγ production in IL-21 treated or mock treated Thp cells.

The results are shown in FIGS. 2A and 2B. For the results shown in FIG. 2A, cells were cultured for one week in the presence of IL-21 or mock sup ematants. Cytokine production was assessed by intracellular cytokine staining four hours after restimulation with PMA/Ionomycin. Results are representative of at least ten experiments.

As with IL-4, addition of IL-21 to neutral and Th1 cultures resulted in a marked reduction in the number of IFNγ producing cells (FIG. 2A, neutral and Th1 conditions). The decreased number of IFNγ producing cells in Th1 cultures was confirmed by ELISPOT analysis. However, unlike what was observed with IL-4, IL-21 by itself was unable to potentiate the production of IL-4 producing Th2 cells (FIG. 2A, neutral condition). IL-21 treatment had no stimulating or inhibitory effect on the generation of IL-4 producing cells under Th2 skewing conditions (FIG. 2A, Th2).

The ability of IL-21 to affect IFNγ production from recently stimulated Thp cells was determined. Purified naïve Thp cells were cultured under neutral and Th1 conditions in the presence or absence of IL-21 for 48 hours. The resulting culture supernatants were examined for IFNγ production using ELISA. It was found that IL-21 reduced the amount of IFNγ produced early in differentiating cultures (FIG. 2B). Therefore, the presence of IL-21 during Th priming affects the ability of both differentiating Th1 cells and effector cells to produce IFNγ.

Example 4

IL-21 does not Directly Inhibit IFNγ Production from Th1 Effector Cells

Figure 3A:
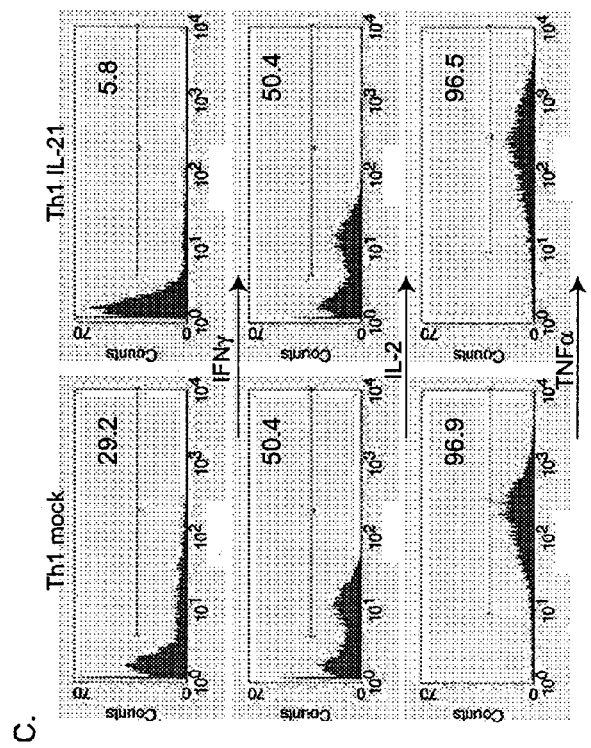
FIG. 3A is a graphic representation of IL-4 and IFNγ production in Thp cells cultured under Th1 skewing conditions in the presence or absence of IL-21.

To determine whether IL-21 directly represses production of IL-21, or instead affects differentiation of IFNγ cells, purified naive Thp cells were cultured under Th1 skewing conditions. IL-21 or mock supernatant was added either at the beginning of culture (Day 0) or 24 hours before restimulation and analysis (Day 5). Cytokine production was assessed by intracellular cytokine staining. The results are shown in FIG. 3A.

Unlike what was observed when IL-21 was added at Day 0, the addition of IL-21 to Th1 cultures at the end of the differentiation period had no effect on IFNγ production, even though Th1 cells express IL-21R and are responsive to IL-21. This finding demonstrates the IL-21 impairs the ability of Thp cell differentiation into IFNγ-producing Th1 cells, but does not directly inhibit IFNγ production from Th1 effector cells.

Example 5

IL-21 Inhibition of IFNγ is Independent of Stat6

The ability of IL-4 to inhibit the differentiation of Th1 cells depends on the expression of Stat6 (Kaplan, M. H., et al., Immunity 4: 313-9, 1996, Takeda, K. et al., Nature 380: 627-30 1996, and Shimoda, K. et al., Nature 380: 630-3, 1996).

In order to determine whether IL-21 mediated inhibition of IFNγ production is also dependent on Stat6, the ability of IL-21 to influence Th1 differentiation in cells lacking Stat6 was determined. Thp cells purified from wild-type or Stat6-deficient mice were cultured for one week under Th1 skewing conditions in the presence of IL-21 or mock supernatant. Cytokine production was assessed by intracellular cytokine staining.

Figure 3B:
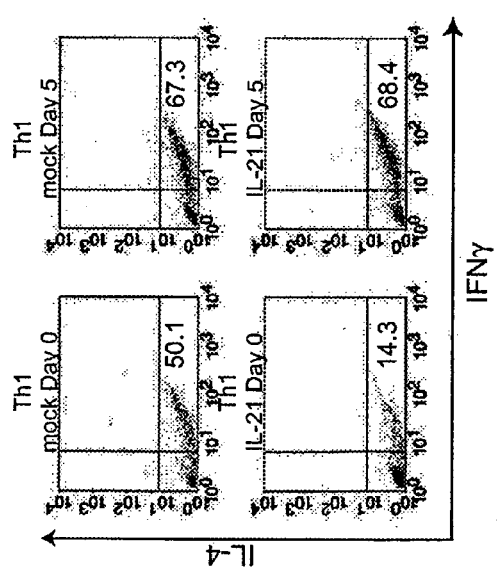
FIG. 3B is a graphic representation of IL-4 and IFNγ production in IL-21 treated or mock treated Thp cells treated in Th1 skewing conditions from wild-type and Stat6−/− mice.

The results are shown in FIG. 3B. In the absence of Stat6, IL-21 was just as effective in preventing the generation of IFNγ producing cells as in the presence of Stat6. Therefore, unlike IL-4, IL-21 does not depend on Stat6 signaling to prevent the generation of IFNγ producing Th1 cells. Additionally, these results demonstrate that the repression of IFNγ induced by IL-21 is not mediated directly through the action of IL-4.

Example 6

IL-21 does not Inhibit other Th1 Cytokines

To determine if IL-21 affects aspects of Th1 development in addition to inhibition of IFNγ production, the ability of IL-21 treated Th1 cells to produce other Th1-associated cytokines was examined.

Thp cells were cultured under Th1 skewing conditions in the presence of IL-21, or of mock supernatants, after which they were assessed for cytokine production by intracellular cytokine staining after secondary stimulation.

Figure 3C:
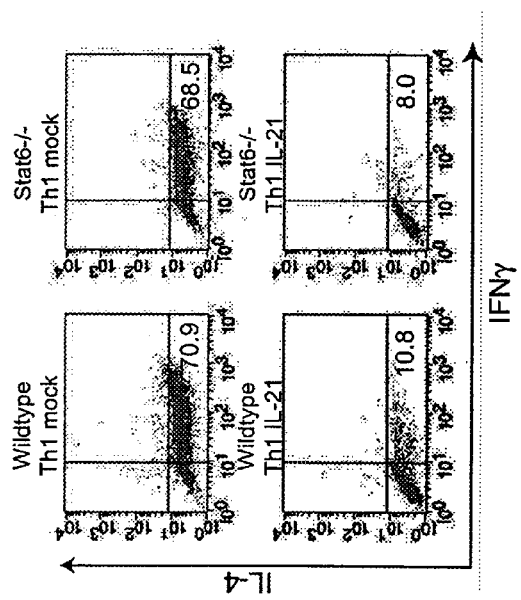
FIG. 3C is a graphic representation of IFNγ, IL-2, and TNFα expression in IL-21 treated or mock treated Th1 cells from wild-type and Stat6−/−mice.

The results are shown in FIG. 3C. Surprisingly, although the number of IFNγ producing cells is significantly reduced when IL-21 is included in the priming conditions, the same cell population had normal numbers of IL-2 and TNFα producing cells. These results demonstrate that that although IL-21 efficiently suppresses the ability of Th1 cells to produce IFNγ, the same cells maintain the capacity to produce Th1 cells and do not default to produce Th2 cytokines.

Example 7

T-bet Expression is Unaffected by IL-21

T-bet is a recently identified transcription factor that is specifically expressed in differentiating Th1 cells and which is also capable of potently inducing IFNγ. To determine if IL-21 treatment of differentiating Th1 cells affected the induction of T-bet expression in Th cells, Thp cells were cultured under Th1 or Th2 skewing conditions. Protein extracts were harvested at the beginning (naive) and 48 hours after culture (Th1 and Th2). T-bet and actin expression were determined by western blot.

Figures 4A, 4B, 4C, 4D:
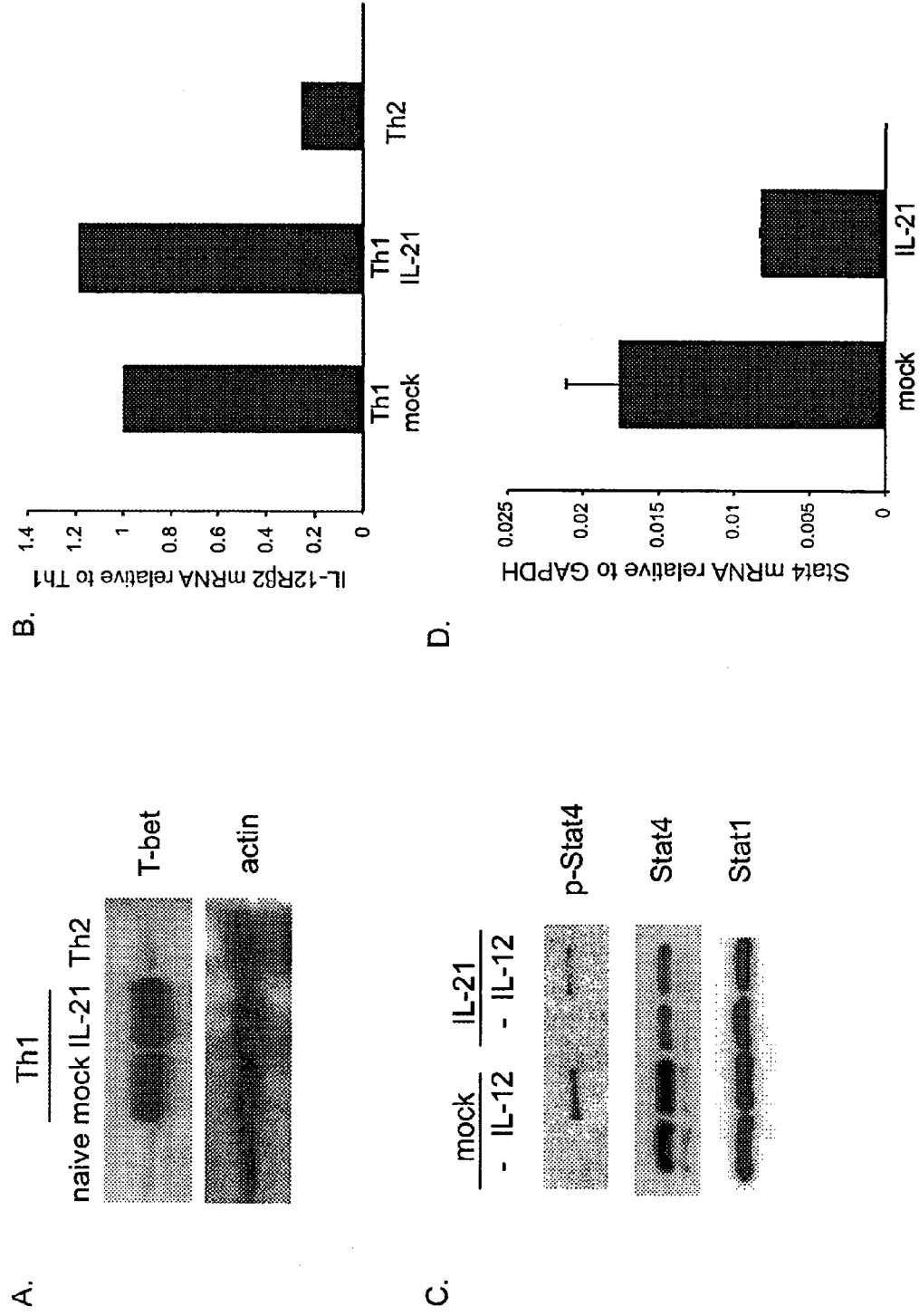
FIG. 4A is a representation of a western blot analysis of T-bet and actin protein levels in Thp cells cultured under Th1 or Th2 skewing conditions.
FIG. 4B is a histogram showing levels of IL-12Rβ32 mRNA relative to levels in Th1 cells.
FIG. 4C is a representation of a western blot analysis of phosphorylated Stat4, Stat4, Stat1, and IL-12 polypeptide levels in Thp cells stimulated with anti-CD3 in the presence of IL-21 or mock supernatants.
FIG. 4D is a histogram showing levels of Stat4 mRNA relative to GAPDH mRNA in mock treated and IL-21 Thp cells stimulated with anti-CD3 for 48 hours in the presence of IL-21 or mock supernatants. IL-4 mRNA and IFNγ.

The results are shown in FIG. 4A. IL-21 or mock supernatants were included in the indicated cultures. As expected, T-bet expression was induced in Th1 cultures and remained low under Th2 conditions. Addition of IL-21 had no effect on T-bet expression in Th1 cells. This result indicates that IL-21-mdiated expression of IFNγ expression is not a result of reduced T-bet expression.

Example 8

IL-21 Inhibits IL-12 Signaling

IL-12 signaling is reported to play an important role in the development of Th1 cells. Th cells lacking IL-12R are severely compromised in their ability to produce IFNγ (Wu, C., et al., J Immunol 159: 1658-65, 1997). Additionally, IL-12Rβ2 chain expression is specifically extinguished in developing Th2 cells, an effect mediated by IL-4 (Szabo, S. J., et al., J Exp Med 185: 817-24, 1997). In order to determine if IL-21, like IL-4, affects the expression of IL-12b2 chain in Th1 cells, RNA from naïve Thp cells cultured under Th1 and Th2 skewing conditions in the presence and absence of IL-21 was analyzed for 12Rβ2 expression by RealTime PCR. Thp cells were cultured under Th 1 or Th2 skewing conditions for one week. IL-21 or mock supernatant was included in indicated cultures. RNA was harvested 24 hours after secondary stimulation with anti-CD3 and assessed for IL-12RP2 expression by Real-Time PCR.

The results are shown in FIG. 4B. The results are representative of three independent experiments. As expected, IL-12Rβ2expression was high in Th1 cells when compared to Th2 cells. However, addition of IL-21 to the Th1 cultures did not affect IL-12Rβ2 expression. Therefore, unlike results reported for IL-4, IL-21 did not cause decreased expression of IL-12Rβ2. Moreover, the high IL-12Rβ2 expression coupled with high TNFα and IL-2 levels suggest that IL-21 treated Th1 cells maintain many Th1 characteristics with the distinct exception of decreased IFNγ production.

Stat4 is specifically activated by IL-12 and is reported to be a critical mediator for the generation of IFNγ producing Th1 cells (Wurster, A. L., et al., Oncogene 19: 2577-84, 2000). In order to determine if IL-21 affects the ability of IL-12 to activate STAT-4, naïve Thp cells were activated for 48 hours in the presence or absence of IL-21. The cells were subsequently stimulated with IL-12, and the extent of Stat4 phosphorylation was determined by western blot analysis. Thp cells were stimulated with anti-CD3 for 48 hours in the presence of IL-21 or mock supernatants. Protein extracts were assessed for phosphorylated Stat4 (p-Stat4), Stat4 and Stat1 by western blot. Results are representative of four independent experiments.

The results are shown in FIG. 4C. Although IL-21 treated cells were found to express normal levels of IL-12Rβ2, Stat4 phosphorylation in response to IL-12 stimulation was reduced in IL-21 treated cells. The decreased levels of phosphorylated Stat4 is also reflected by a decrease in total Stat4 protein levels. As a comparison, Stat1 protein was unaffected by IL-21 treatment.

Stat4 RNA levels were also examined. Thp cells were cultured as described for FIG. 4C, after which RNA was harvested and assessed for Stat4 expression in duplicate by RealTime PCR.

The results are shown in FIG. 4D. Results are representative of three independent experiments. Lower levels of Stat4RNA levels were detected. The IL-21 induced decrease in Stat4 protein levels is likely due to a decrease in Stat4 mRNA. These findings suggest that IL-21 hinders the responsiveness of developing Th1 cells to IL-12 through a reduction of Stat4 gene expression.

Example 9

IL-21 Signaling is Required for Limiting a Th1 Response in vivo

To determine if endogenously produced IL-21 plays a role in limiting Th1 cell function in vivo, the extent of delayed-type hypersensitivity response (DTH) was examined in IL-21R-deficient mice. DTH is a classic Th1 cell-mediated inflammatory response. IL-21R-deficient mice backcrossed on the C57BL/6 background were generated as described in Kasian et al., Immunity 16:559-60, 2002. Eight week old male mice were immunized subcutaneously with 100 mg TNP-KLH (2,4,6-trinitrophenyl-keyhole limpet hemocyanin; Biosearch Technologies, Novato, Calif.) emulsified in DFA at the tail base. After six days mice were challenged with 50 μg of TNP-KLH in one hind footpad and PBS in the contralateral hind footpad. Footpad thickness was measured 24 hours after challenge.

Figure 5A:
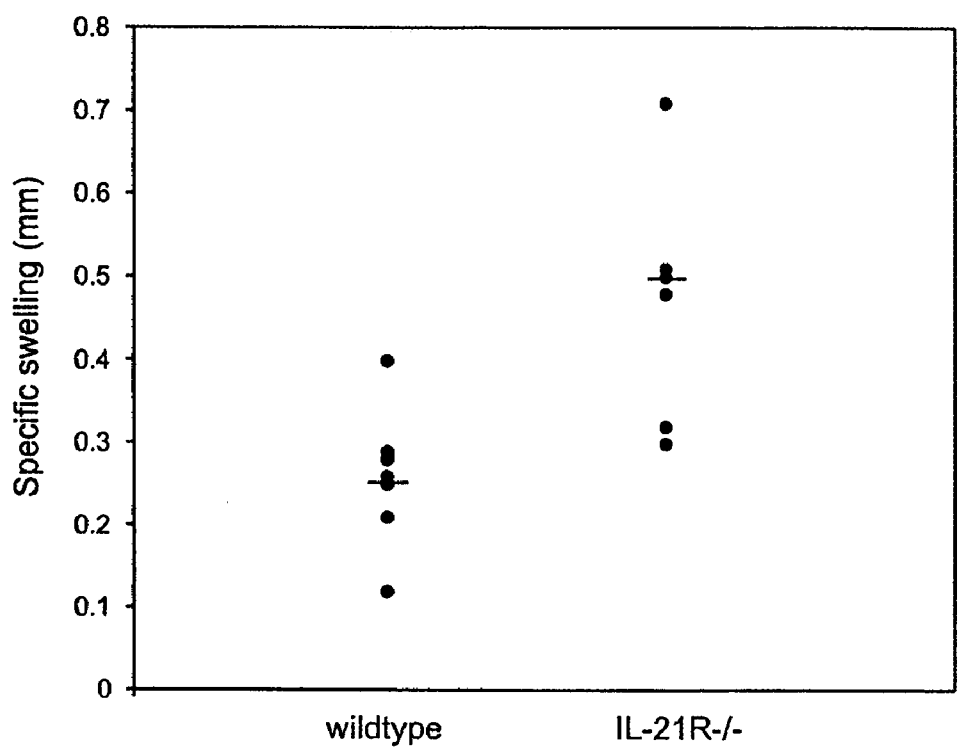
FIG. 5A is a graph showing specific swelling in TNP-KLH-immunized wild type and IL-21R−/− mice subsequently injected with TNP-KLH or PBS.

The results are presented in FIG. 5A. Specific footpad swelling of wild type and IL-21R-deficient (IL-21R-/-) mice was determined by subtracting nonspecific swelling the PBS-injected footpad from TNP-KLH-induced swelling. Each data point represents one mouse. Horizontal lines indicate averages. Results reflect pooling of data from two independent experiments. The results demonstrate that wild type animals responded to antigenic challenge with robust swelling of the footpad. Surprisingly, IL-21R-deficient mice mounted a much stronger DTH response, resulting in an average of twice the swelling.

Figure 5B:
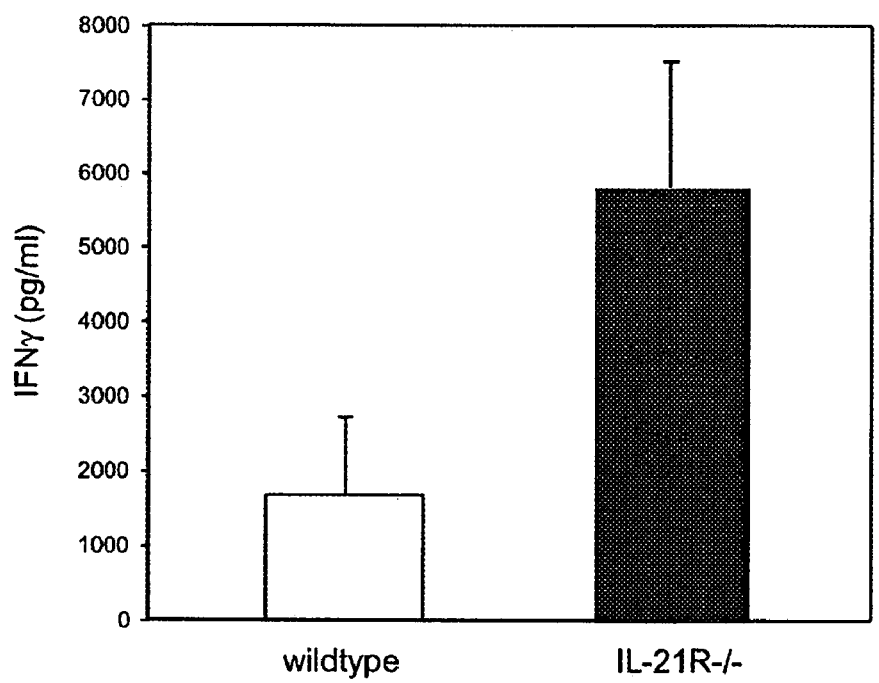
FIG. 5B is a histogram showing IFNγ production in CD4+T cells purified from draining lymph nodes of TNP-KLH-immunized wild type and IL-21R−/− mice restimulated by antigen.

IFNγ production was also examined in immunized mice. The results are shown in FIG. 5B. Purified CD4+ T cells from draining lymph nodes of immunized mice were stimulated in vitro with 250 mg/ml TNP-KLH. Supernatants were analyzed for IFNγ levels by ELISA. Results shown are the average of data from two mice from each genotype performed in duplicate. The increased DTH response in IL-21R-deficient animals correlated with a marked increase in IFNγ production from CD4+ cells purified from the draining lymph nodes and restimulated by antigen in vitro.

These results demonstrate that IL-21 is involved in limiting TH1 cell responses by suppressing the production of IFNγ.

Additional embodiments are within the claims.

What is claimed is:

1. A method for inhibiting or reducing differentiation of a Th precursor (Thp) cell or cell population into a Th2 cell or cell population, comprising contacting said Thp cell or cell population from a subject or sample of interest with an antagonist of IL-21 or IL-21R in an amount sufficient to inhibit or reduce the differentiation, wherein the inhibition or reduction of the differentiation is measured by comparing the level of Th2 cells in the contacted cell or cell population from the subject or sample of interest to the level of Th2 cells in a control subject or sample, and wherein the antagonist is selected from the group consisting of an anti-IL-21R antibody, an antigen-binding fragment of an anti-IL-21R antibody and a soluble IL-21R, wherein the soluble IL-21R comprises an extracellular domain of an IL-21R that is capable of binding IL-21 or a fragment thereof, and wherein the extracellular domain of the soluble IL-21R is at least 90% identical to amino acids 20-235 of SEQ ID NO:4.

2. A method for increasing interferon gamma (IFNγ) levels in a T cell or cell population, comprising contacting said T cell or cell population from a subject or sample of interest with an antagonist of IL-21 or IL-21R in an amount sufficient to increase IFNγ levels in said T cell or cell population, wherein the increase in IFNγ levels is measured by comparing the level of IFNγ in the T cell or cell population from the subject or sample of interest to the level of IFNγ in a T cell or cell population from a control subject or sample, and wherein the antagonist is selected from the group consisting of an anti-IL-21R antibody, an antigen-binding fragment of an anti-IL-21R antibody and a soluble IL-21R, wherein the soluble IL-21R comprises an extracellular domain of an IL-21R that is capable of binding IL-21 or a fragment thereof, and wherein the extracellular domain of the soluble IL-21R is at least 90% identical to amino acids 20-235 of SEQ ID NO:4.

3. The method of either claim 1 or 2, wherein the antagonist of IL-21 or IL-21 R is a soluble IL-21R, and wherein the extracellular domain of the soluble IL-21R comprises amino acids 1 to 235 of SEQ ID NO:4 or amino acids 20 to 235 of SEQ ID NO:4.

4. The method of claim 3, wherein the soluble IL-21R further comprises an Fc fragment.

5. The method of either claim 1 or 2, wherein the antagonist is an anti-IL-21R antibody or an antigen-binding fragment thereof.

6. The method of claim 2, wherein the T cell or cell population comprises at least one Th1 cell.

7. The method of either claim 1 or 2, wherein the contacting step is carried out ex vivo, in vitro or in vivo.

8. The method of claim 7, wherein the contacting step is carried out in a mammalian subject.

9. The method of claim 8, wherein the mammalian subject is a human.

10. A method for inhibiting or reducing the differentiation of a Thp cell or cell population into a Th2 cell or cell population in a subject in need thereof, comprising administering to the subject an antagonist of IL-21 or IL-21R selected from the group consisting of an anti-IL-21R antibody, an antigen-binding fragment of an anti-IL-21R antibody and a soluble IL-21R, wherein the soluble IL-21R comprises an extracellular domain of an IL-21R that is capable of binding IL-21 or a fragment thereof, and wherein the extracellular domain of the soluble IL-21R is at least 90% identical to amino acids 20-235 of SEQ ID NO:4.

11. A method for increasing interferon gamma (IFNγ) levels in a T cell or cell population in a subject in need thereof, comprising administering to the subject an antagonist of IL-21 or IL-21R selected from the group consisting of an anti-IL-21R antibody, an antigen-binding fragment of an anti-IL-21R antibody and a soluble IL-21R, wherein the soluble IL-21R comprises an extracellular domain of an IL-21R that is capable of binding IL-21 or a fragment thereof, and wherein the extracellular domain of the soluble IL-21R is at least 90% identical to amino acids 20-235 of SEQ ID NO:4.

* * * * *

UNITED STATES PATENT AND TRADEMARK OFFICE
CERTIFICATE OF CORRECTION

PATENT NO. : 7,314,623 B2
APPLICATION NO. : 10/620169
DATED : January 1, 2008
INVENTOR(S) : Michael J. Grusby et al.

It is certified that error appears in the above-identified patent and that said Letters Patent is hereby corrected as shown below:

<u>COLUMN 1</u>

Line 57, "basedin" should read --based in--.

<u>COLUMN 3</u>

Line 12, "Receptor." should read --receptor.--;
    Line 22, "subject," should read --subject;--; and
    Line 36, "Receptor." should read --receptor.--.

<u>COLUMN 4</u>

Line 32, "IL-12R$\beta$32" should read --IL-12R$\beta$2--.

<u>COLUMN 16</u>

Line 45, "Theses" should read --These--.

<u>COLUMN 18</u>

Line 14, "a" should read --an--; and
    Line 26, "a" should read --an--.

<u>COLUMN 19</u>

Line 16, "a" should read --an--.

UNITED STATES PATENT AND TRADEMARK OFFICE
CERTIFICATE OF CORRECTION

| | | |
|---|---|---|
| PATENT NO. | : 7,314,623 B2 | |
| APPLICATION NO. | : 10/620169 | |
| DATED | : January 1, 2008 | |
| INVENTOR(S) | : Michael J. Grusby et al. | |

It is certified that error appears in the above-identified patent and that said Letters Patent is hereby corrected as shown below:

<u>COLUMN 29</u>

Line 28, "I1-21" should read --IL-21--.

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,314,623 B2 Page 1 of 1
APPLICATION NO. : 10/620169
DATED : January 1, 2008
INVENTOR(S) : Michael J. Grusby et al.

It is certified that error appears in the above-identified patent and that said Letters Patent is hereby corrected as shown below:

ON COVER PAGE AT (73) ASSIGNEE

Insert --Assignees: Wyeth, Madison, NJ (US); The President and Fellows of Harvard College, Cambridge, MA (US)--.

Signed and Sealed this

Third Day of February, 2009

JOHN DOLL
*Acting Director of the United States Patent and Trademark Office*

SEQUENCE LISTING

<160> NUMBER OF SEQ ID NOS: 13

<210> SEQ ID NO 1
<211> LENGTH: 617
<212> TYPE: DNA
<213> ORGANISM: Homo sapiens

<400> SEQUENCE: 1

```
gctgaagtga aaacgagacc aaggtctagc tctactgttg gtacttatga gatccagtcc      60
tggcaacatg gagaggattg tcatctgtct gatggtcatc ttcttgggga cactggtcca     120
caaatcaagc tcccaaggtc aagatcgcca catgattaga atgcgtcaac ttatagatat     180
tgttgatcag ctgaaaaatt atgtgaatga cttggtccct gaatttctgc cagctccaga     240
agatgtagag acaaactgtg agtggtcagc ttttttcctgc tttcagaagg cccaactaaa     300
gtcagcaaat acaggaaaca atgaaaggat aatcaatgta tcaattaaaa agctgaagag     360
gaaaccacct tccacaaatg cagggagaag acagaaacac agactaacat gcccttcatg     420
tgattcttat gagaaaaaac cacccaaaga attcctagaa agattcaaat cacttctcca     480
aaagatgatt catcagcatc tgtcctctag aacacacgga agtgaagatt cctgaggatc     540
taacttgcag ttggcactaa tgttacatac tctaatatag tagtgaaagt catttctttg     600
tattccaagt ggaggag                                                    617
```

<210> SEQ ID NO 2
<211> LENGTH: 162
<212> TYPE: PRT
<213> ORGANISM: Homo sapiens

<400> SEQUENCE: 2

```
Met Arg Ser Ser Pro Gly Asn Met Glu Arg Ile Val Ile Cys Leu Met
  1               5                  10                  15

Val Ile Phe Leu Gly Thr Leu Val His Lys Ser Ser Gln Gly Gln
             20                  25                  30

Asp Arg His Met Ile Arg Met Arg Gln Leu Ile Asp Ile Val Asp Gln
         35                  40                  45

Leu Lys Asn Tyr Val Asn Asp Leu Val Pro Glu Phe Leu Pro Ala Pro
     50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Asn Glu Arg Ile Ile
                 85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser
```

<210> SEQ ID NO 3
<211> LENGTH: 2887
<212> TYPE: DNA
<213> ORGANISM: Homo sapiens -continued

```
<400> SEQUENCE: 3
gaagcagcag gtaccccctc cacatcccta gggctctgtg atgtaggcag aggcccgtgg      60
gagtcagcat gccgcgtggc tgggccgccc ccttgctcct gctgctgctc cagggaggct     120
ggggctgccc cgacctcgtc tgctacaccg attacctcca gacggtcatc tgcatcctgg     180
aaatgtggaa cctccacccc agcacgctca cccttacctg gcaagaccag tatgaagagc     240
tgaaggacga ggccacctcc tgcagcctcc acaggtcggc ccacaatgcc acgcatgcca     300
cctacacctg ccacatggat gtattccact tcatggccga cgacattttc agtgtcaaca     360
tcacagacca gtctggcaac tactcccagg agtgtggcag cttttctcctg gctgagagca     420 tcaagccggc tccccctttc aacgtgactg tgaccttctc aggacagtat aatatctcct     480
ggcgctcaga ttacgaagac cctgccttct acatgctgaa gggcaagctt cagtatgagc     540
tgcagtacag gaaccgggga gacccctggg ctgtgagtcc gaggagaaag ctgatctcag     600
tggactcaag aagtgtctcc ctcctccccc tggagttccg caaagactcg agctatgagc     660
tgcaggtgcg ggcagggccc atgcctggct cctcctacca ggggacctgg agtgaatgga     720
gtgacccggt catctttcag acccagtcag aggagttaaa ggaaggctgg aaccctcacc     780
tgctgcttct cctcctgctt gtcatagtct tcattcctgc cttctggagc ctgaagaccc     840
atccattgtg gaggctatgg aagaagatat gggccgtccc cagccctgag cggttcttca     900
tgcccctgta caagggctgc agcggagact caagaaatg gtgggtgca cccttcactg     960 gctccagcct ggagctggga ccctggagcc cagaggtgcc ctccaccctg gaggtgtaca    1020
gctgccaccc accacggagc ccggccaaga ggctgcagct cacggagcta caagaaccag    1080
cagagctggt ggagtctgac ggtgtgccca agcccagctt ctggccgaca gcccagaact    1140
cggggggctc agcttacagt gaggagaggg atcggccata cggcctggtg tccattgaca    1200
cagtgactgt gctagatgca gaggggccat gcacctggcc ctgcagctgt gaggatgacg    1260
gctacccagc cctggacctg gatgctggcc tggagcccag cccaggccta gaggacccac    1320
tcttggatgc agggaccaca gtcctgtcct gtggctgtgt ctcagctggc agccctgggc    1380
taggagggcc cctgggaagc ctcctggaca gactaaagcc accccttgca gatggggagg    1440
actgggctgg gggactgccc tggggtggcc ggtcacctgg aggggtctca gagagtgagg    1500
cgggctcacc cctggccggc ctggatatgg acacgtttga cagtggcttt gtgggctctg    1560
actgcagcag ccctgtggag tgtgacttca ccagccccgg ggacgaagga cccccccgga    1620
gctacctccg ccagtggggtg gtcattcctc cgccactttc gagccctgga ccccaggcca    1680
gctaatgagg ctgactggat gtccagagct ggccaggcca ctgggccctg agccagagac    1740
aaggtcacct gggctgtgat gtgaagacac ctgcagcctt tggtctcctg gatgggcctt    1800
tgagcctgat gtttacagtg tctgtgtgtg tgtgtgcata tgtgtgtgtg tgcatatgca    1860
tgtgtgtgtg tgtgtgtgtc ttaggtgcgc agtggcatgt ccacgtgtgt gtgtgattgc    1920
acgtgcctgt gggcctggga taatgcccat ggtactccat gcattcacct gccctgtgca    1980
tgtctggact cacggagctc acccatgtgc acaagtgtgc acagtaaacg tgtttgtggt    2040
caacagatga caacagccgt cctccctcct agggtcttgt gttgcaagtt ggtccacagc    2100
atctccgggg ctttgtggga tcagggcatt gcctgtgact gaggcggagc ccagccctcc    2160
agcgtctgcc tccaggagct gcaagaagtc catattgttc cttatcacct gccaacagga    2220
agcgaaaggg gatggagtga gcccatggtg acctcgggaa tggcaatttt ttgggcggcc    2280
cctggacgaa ggtctgaatc ccgactctga taccttctgg ctgtgctacc tgagccaagt    2340
```

-continued

```
cgcctcccct ctctgggcta gagtttcctt atccagacag tggggaaggc atgacacacc      2400
tgggggaaat tggcgatgtc acccgtgtac ggtacgcagc ccagagcaga ccctcaataa      2460
acgtcagctt ccttccttct gcggccagag ccgaggcggg cggggtgag aacatcaatc       2520 gtcagcgaca gcctgggcac ccgcggggcc gtcccgcctg cagagggcca ctcgggggggg    2580 tttccaggct taaaatcagt ccgtttcgtc tcttggaaac agctccccac caaccaagat     2640
ttctttttct aacttctgct actaagtttt taaaaattcc ctttatgcac caagagata     2700 tttattaaac accaattacg tagcaggcca tggctcatgg gacccacccc ccgtggcact     2760
catggagggg gctgcaggtt ggaactatgc agtgtgctcc ggccacacat cctgctgggc     2820 cccctacccct gccccaattc aatcctgcca ataaatcctg tcttatttgt tcatcctgga   2880
gaattga                                                               2887
```

<210> SEQ ID NO 4
<211> LENGTH: 538
<212> TYPE: PRT
<213> ORGANISM: Homo sapiens

<400> SEQUENCE: 4

```
Met Pro Arg Gly Trp Ala Ala Pro Leu Leu Leu Leu Leu Gln Gly
  1               5                  10                  15

Gly Trp Gly Cys Pro Asp Leu Val Cys Tyr Thr Asp Tyr Leu Gln Thr
                 20                  25                  30

Val Ile Cys Ile Leu Glu Met Trp Asn Leu His Pro Ser Thr Leu Thr
             35                  40                  45

Leu Thr Trp Gln Asp Gln Tyr Glu Glu Leu Lys Asp Glu Ala Thr Ser
         50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Asp Ile Phe Ser Val
                 85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270
```

-continued

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
            370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
            450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
                500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
            530                 535

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Pro Leu Leu Leu Leu Leu Leu Leu Pro Ser Pro Leu His Pro
  1               5                   10                  15

<210> SEQ ID NO 6
<211> LENGTH: 224
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

His Thr Cys Pro Pro Cys Pro Ala Pro Glu Ala Leu Gly Ala Pro Ser
  1               5                   10                  15

```
Val Phe Leu Phe Pro Lys Pro Lys Asp Thr Leu Met Ile Ser Arg
         20                  25                  30

Thr Pro Glu Val Thr Cys Val Val Asp Val Ser His Glu Asp Pro
             35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Val Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
aagattcctg aggatccgag aag                                            23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gcattcgtga gcgtctatag tgtc                                           24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ttcccgagga ctgaggagac gcc                                            23
```

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
tttccatttt tgcatcaagt tctc                                          24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ccgatctaga gtcagccgct                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
aaacctgagc ccaacgacaa                                               20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
agtgtccgtt tgcaccgtc                                                19
```